(12) United States Patent
Dieterle et al.

(10) Patent No.: US 8,202,814 B2
(45) Date of Patent: Jun. 19, 2012

(54) PROCESS FOR REGENERATING A CATALYST BED DEACTIVATED IN THE COURSE OF A HETEROGENEOUSLY CATALYZED PARTIAL DEHYDROGENATION OF A HYDROCARBON

(75) Inventors: Martin Dieterle, Jersey City, NJ (US); Götz-Peter Schindler, Ludwigshafen (DE); Catharina Horstmann, Ludwigshafen (DE); Klaus Joachim Müller-Engel, Stutensee (DE)

(73) Assignee: BASF SE, Ludwigshafen (DE)

( * ) Notice: Subject to any disclaimer, the term of this patent is extended or adjusted under 35 U.S.C. 154(b) by 1112 days.

(21) Appl. No.: 12/025,448

(22) Filed: Feb. 4, 2008

(65) Prior Publication Data

US 2008/0188695 A1    Aug. 7, 2008

Related U.S. Application Data

(60) Provisional application No. 60/888,366, filed on Feb. 6, 2007.

(30) Foreign Application Priority Data

Feb. 6, 2007 (DE) .......... 10 2007 006 647

(51) Int. Cl.
*B01J 38/04* (2006.01)
(52) U.S. Cl. .......... 502/34
(58) Field of Classification Search .......... None
See application file for complete search history.

(56) References Cited

U.S. PATENT DOCUMENTS

| 5,705,684 | A | 1/1998 | Hefner et al. |
| 6,426,433 | B1 | 7/2002 | Machhammer et al. |
| 6,781,017 | B2 | 8/2004 | Machhammer et al. |
| 6,987,078 | B2 * | 1/2006 | Kelly et al. .......... 502/38 |
| 7,154,009 | B2 | 12/2006 | Dieterle et al. |
| 7,211,692 | B2 | 5/2007 | Dieterle et al. |
| 7,214,822 | B2 | 5/2007 | Borgmeier et al. |
| 7,238,827 | B2 | 7/2007 | Hechler et al. |
| 7,291,761 | B2 | 11/2007 | Machhammer et al. |
| 7,321,058 | B2 | 1/2008 | Machhammer et al. |
| 7,348,443 | B2 * | 3/2008 | Proll et al. .......... 549/523 |

(Continued)

FOREIGN PATENT DOCUMENTS

DE    100 28 582 A1    12/2001

(Continued)

OTHER PUBLICATIONS

Russian Office Action issued Jul. 13, 2011, in Patent Application No. 2009133170/04 (English-language translation only).

*Primary Examiner* — Melvin C Mayes
*Assistant Examiner* — Stefanie Cohen
(74) *Attorney, Agent, or Firm* — Oblon, Spivak, McClelland, Maier & Neustadt, L.L.P.

(57) ABSTRACT

A process for regenerating a catalyst bed deactivated in the course of a heterogeneously catalyzed partial dehydrogenation of a hydrocarbon, in which a gas comprising molecular oxygen is conducted at elevated temperature through the deactivated catalyst bed and, in the course of the regeneration, the content of molecular oxygen in the regeneration gas is increased repeatedly and the increase in the carbon oxide content of the regeneration gas as it flows through the deactivated catalyst bed is restricted to values of $\leq 5\%$ by volume.

22 Claims, 2 Drawing Sheets

U.S. PATENT DOCUMENTS

| | | |
|---|---|---|
| 7,388,109 B2 | 6/2008 | Machhammer et al. |
| 2004/0199001 A1 | 10/2004 | Schindler et al. |
| 2005/0096483 A1 | 5/2005 | Dieterle et al. |
| 2007/0142689 A1 | 6/2007 | Hechler et al. |
| 2007/0276157 A1 | 11/2007 | Machhammer et al. |
| 2007/0299278 A1 | 12/2007 | Hechler et al. |
| 2008/0045685 A1 | 2/2008 | Dieterle et al. |
| 2008/0119673 A1 | 5/2008 | Hechler et al. |

FOREIGN PATENT DOCUMENTS

| | | |
|---|---|---|
| DE | 102 45 585 A1 | 4/2004 |
| DE | 103 16 039 A1 | 10/2004 |
| DE | 10 2004 032 129 A1 | 3/2005 |
| DE | 103 50 812 A1 | 6/2005 |
| DE | 103 50 822 A1 | 6/2005 |
| DE | 103 51 269 A1 | 6/2005 |
| DE | 10 2005 013 039 A1 | 9/2006 |
| DE | 10 2005 061 626 A1 | 6/2007 |
| DE | 10 2006 017 623 A1 | 10/2007 |
| DE | 10 2006 024 901 A1 | 11/2007 |
| DE | 10 2006 029 790 A1 | 1/2008 |
| DE | 10 2006 035 718 A1 | 1/2008 |
| EA | 004599 B1 | 6/2004 |
| EA | 006040 B1 | 8/2005 |
| EP | 0 731 077 A2 | 9/1996 |
| EP | 0 799 169 | 10/1997 |
| EP | 1 642 879 A1 | 4/2006 |
| RU | 2 113 902 C1 | 6/1998 |
| RU | 2 159 676 C1 | 11/2000 |
| WO | WO 96/19424 | 6/1996 |
| WO | WO 00/10961 | 3/2000 |
| WO | WO 01/96008 A1 | 12/2001 |
| WO | WO 01/96270 A2 | 12/2001 |
| WO | WO 01/96271 A2 | 12/2001 |
| WO | WO 02/26668 A1 | 4/2002 |
| WO | WO 02/45852 A2 | 6/2002 |
| WO | WO 03/011804 A2 | 2/2003 |
| WO | WO 03/076370 A1 | 9/2003 |

\* cited by examiner

PROCESS FOR REGENERATING A CATALYST BED DEACTIVATED IN THE COURSE OF A HETEROGENEOUSLY CATALYZED PARTIAL DEHYDROGENATION OF A HYDROCARBON

Figure 1:
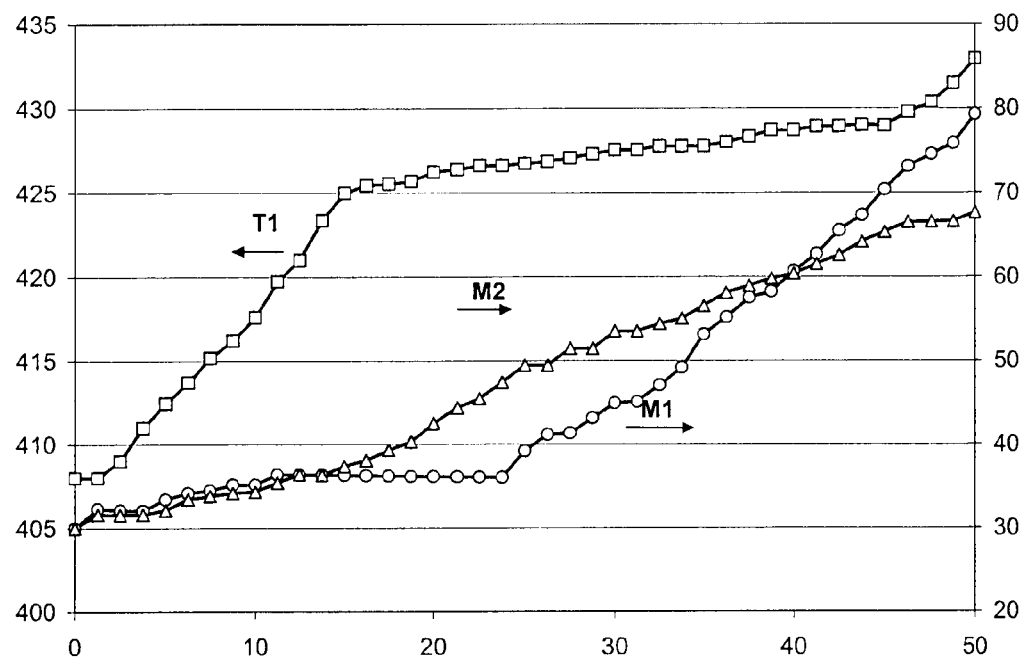
FIG. 1: counteraction of deactivation of overall fixed catalyst bed.

The present invention relates to a process for regenerating a catalyst bed deactivated in the course of a heterogeneously catalyzed partial dehydrogenation of a hydrocarbon to be dehydrogenated to a dehydrogenated hydrocarbon, which comprises, over a period t, the passage of a regeneration gas comprising molecular oxygen and inert gas but no hydrocarbon at elevated temperature through the deactivated catalyst bed with the proviso that the total content $G^A$ of carbon oxides ($CO$, $CO_2$) in the regeneration gas passed through the catalyst bed, when it exits from the catalyst bed, is at least temporarily greater in the course of the regeneration over the period t than the corresponding content $G^E$, in each case expressed in % by volume of the regeneration gas volume, of the same regeneration gas passed through the catalyst bed when it enters the catalyst bed, and the difference $\Delta G = G^A - G^E$ passes through a maximum value $\Delta G^{max}$ by the end of the regeneration process.

The term "dehydrogenated hydrocarbon" used in this application shall comprise hydrocarbons whose molecules comprise at least two ("two" are preferred from an application point of view) hydrogen atoms fewer than the molecules of a hydrocarbon to be dehydrogenated. In addition, the term "hydrocarbon" shall comprise substances whose molecules are composed only of the elements carbon and hydrogen.

Dehydrogenated hydrocarbons thus comprise in particular acyclic and cyclic aliphatic hydrocarbons having one or more C,C double bonds in the molecule.

Examples of such aliphatic dehydrogenated hydrocarbons are propene, isobutene, ethylene, 1-butene, 2-butene and butadiene, and also all pentenes. In other words, the dehydrogenated hydrocarbons include in particular the monounsaturated linear hydrocarbons (n-alkenes) or branched aliphatic hydrocarbons (e.g. isoalkenes), and also the cycloalkenes.

In addition, the dehydrogenated hydrocarbons shall also comprise the alkapolyenes (e.g. dienes and trienes) which comprise more than one carbon-carbon double bond in the molecule. Dehydrogenated hydrocarbons should, though, also comprise hydrocarbon compounds which are obtainable proceeding from alkyl aromatics such as ethylbenzene or isopropylbenzene by dehydrogenating the alkyl substituents. These are, for example, compounds such as styrene or $\alpha$-methylstyrene.

Quite generally, dehydrogenated hydrocarbons are valuable starting compounds for the synthesis of, for example, functionalized, free-radically polymerizable compounds (for example, acrylic acid from propene or methacrylic acid from isobutene and their polymerization products). For example, it is possible to obtain such functionalized compounds by partial oxidation of dehydrogenated hydrocarbons. However, dehydrogenated hydrocarbons are also suitable for the preparation of compounds such as methyl tert-butyl ether (conversion product of isobutene which is suitable, for example, as a fuel additive for adjusting the octane number). However, dehydrogenated hydrocarbons may also themselves be used as such for polymerization.

In this document, useful hydrocarbons to be dehydrogenated include in particular the acyclic and cyclic alkanes, but also olefins (whose number of C, C double bonds is to be increased) (as an example, the heterogeneously catalyzed partial dehydrogenation of n-butenes to butadiene may be mentioned).

In other words, the term "hydrocarbons to be dehydrogenated" in this patent application comprises, for example, hydrocarbons of the stoichiometry $C_nH_{2n+2}$ where $n>1$ to $n\leq20$, and of the stoichiometry $C_nH_{2n}$ where $n>1$ to $n\leq20$, and of the stoichiometry $C_nH_{2n-2}$ where $n>2$ to $n\leq20$, and n=an integer, especially $C_2$- to $C_{16}$-alkanes for example ethane (to ethylene), propane (to propylene), n-butane, isobutane (to isobutene), n-pentane, isopentane, n-hexane, n-heptane, n-octane, n-nonane, n-decane, n-undecane, n-dodecane, n-tridecane, n-tetradecane, n-pentadecane and n-hexadecane.

In particular, though, all statements made in this document apply to $C_2$- to $C_6$-alkanes as hydrocarbons to be dehydrogenated and very particularly to $C_2$- to $C_4$-alkanes as hydrocarbons to be dehydrogenated. In other words, hydrocarbons to be dehydrogenated in this document are in particular ethane, propane, n-butane and isobutane, but also 1-butene and 2-butene and also all pentanes.

In particular, all statements made in this document apply to propane as the hydrocarbon to be dehydrogenated and propylene as the resulting dehydrogenated hydrocarbon, and also to catalysts to be used for this heterogeneously catalyzed dehydrogenation.

Processes for preparing dehydrogenated hydrocarbons are common knowledge (c.f., for example, WO 03/076370, DE-A 10 2004 032 129, EP-A 731 077, WO 01/96271, WO 01/96270, DE-A 103 16 039, WO 03/011804, WO 00/10961, EP-A 799 169, DE-A 102 45 585 and also German applications 10 2005 061626, 10 2006 017 623 and 10 2006 035 718 and DE 102006024901.1).

In principle the processes for preparing dehydrogenated hydrocarbons by heterogeneously catalyzed partial dehydrogenation of at least one hydrocarbon to be dehydrogenated are distinguished in two groups: oxidative and nonoxidative heterogeneously catalyzed partial dehydrogenations. In contrast to the oxidative heterogeneously catalyzed partial dehydrogenation, the nonoxidative (also referred to in this document as "conventional" heterogeneously catalyzed partial dehydrogenation) heterogeneously catalyzed partial dehydrogenation proceeds without involvement of oxygen. In other words, the hydrogen to be pulled from the hydrocarbon to be dehydrogenated is pulled out directly as molecular hydrogen and is not oxidized, even in a subsequent step, at least partly with oxygen to give water. The thermal character of nonoxidative dehydrogenation is thus always endothermic. In oxidative heterogeneously catalyzed partial dehydrogenation, the molecular hydrogen to be pulled from the hydrocarbon to be dehydrogenated is, in contrast, pulled out with involvement of oxygen. This pulling-out can be effected directly as water ($H_2O$) (this case is also referred to, in abbreviated form, as a heterogeneously catalyzed oxydehydrogenation; its thermal character is always exothermic). However, the pulling-out can also be effected initially as molecular hydrogen (i.e. nonoxidatively and conventionally) which is then oxidized in a subsequent step partly or completely with oxygen to water ($H_2O$) (according to the extent of the subsequent hydrogen combustion, the overall thermal character may be endothermic, exothermic or neutral).

What is common to all aforementioned heterogeneously catalyzed partial dehydrogenations of hydrocarbons to be dehydrogenated is that they have to be performed at comparatively high reaction temperatures. Typical reaction temperatures may be ≧250° C., frequently ≧300° C., often ≧350° C., or ≧400° C., or ≧450° C., or ≧500° C.

What is additionally common to all aforementioned heterogeneously catalyzed partial dehydrogenations of hydrocarbons to be dehydrogenated is that, in the course of their long-term operation, increasingly higher reaction temperatures are required with increasing operating time, in order (under otherwise unchanged dehydrogenation conditions) to maintain the dehydrogenation conversion in single pass of the reaction gas mixture through the reaction chamber. Among other reasons, this is typically because there is deposition of carbons and/or high-boiling hydrocarbons on the outer and inner surface of the catalysts used, which blocks access to the active sites of the catalysts, which is normally balanced out from a conversion point of view by increasing the effectiveness of the active sites of the catalysts which remain accessible in each case by increasing the temperature.

WO 01/96008 discloses the interruption of the heterogeneously catalyzed dehydrogenation from time to time in order to remove aforementioned deposits by passing a regeneration gas which comprises molecular oxygen and inert gas but no hydrocarbon at elevated temperature through the catalyst bed, which oxidizes the deposits to carbon oxides. A disadvantage of the teaching of WO 01/96008 is that the regeneration gas according to the teaching of WO 01/96008 comprises 5% molecular oxygen over the entire regeneration time. The regeneration result achievable in this way within a given regeneration time is not satisfactory.

This applies equally to the dehydrogenation method recommended in DE-A 10 2006 029 790 for deactivated oxyde-hydrogenation catalysts, which is based on that for partial oxidation catalysts as described in documents DE-A 10351269, DE-A 10350812 and DE-A 10350822.

DE-A 10028582, DE-A 10 2006 035 718, and DE-A 10 2005 013 039 disclose the performance of the regeneration in such a way that nitrogen-diluted air is first passed over the catalyst bed at a temperature of from 300 to 600° C. in first regeneration stages. The catalyst loading with regeneration gas may be, for example, from 50 to 10 000 $h^{-1}$ and the oxygen content of the regeneration gas from 0.1 or 0.5 to 20% by volume. In subsequent further regeneration stages the regeneration gas used may be air under otherwise identical regeneration conditions.

A disadvantage of both documents is that they do not comprise any specific embodiment of the regeneration method recommended.

It was therefore an object of the present invention to provide a regeneration process as described at the outset, which causes firstly increased efficiency and secondly increased effectiveness.

Moreover, the deactivation behavior of the regenerated catalyst bed should essentially not differ from the deactivation behavior of the freshly charged catalyst bed. This is generally not the case in the prior art processes.

Accordingly, a process has been found for regenerating a catalyst bed deactivated in the course of a heterogeneously catalyzed partial dehydrogenation of a hydrocarbon to be dehydrogenated to a dehydrogenated hydrocarbon, which comprises, over a period t, the passage of a regeneration gas comprising molecular oxygen and inert gas but no hydrocarbon at elevated temperature through the deactivated catalyst bed with the proviso that the total content $G^A$ of carbon oxides in the regeneration gas passed through the catalyst bed, when it exits from the catalyst bed, is at least temporarily greater in the course of the regeneration over the period t than the corresponding content $G^E$, in each case expressed in % by volume of the regeneration gas volume, of the same regeneration gas passed through the catalyst bed when it enters the catalyst bed, and the difference $\Delta G = G^A - G^E$ passes through a maximum value $\Delta G^{max}$ by the end of the regeneration process, wherein a) 0.2% by volume ≦ $\Delta G^{max}$ ≦ 5% by volume and
b) the content of molecular oxygen in the regeneration gas to be passed through the catalyst bed, expressed in % by volume of the regeneration gas volume, is increased at least three times during the period t up to the end of the regeneration process and each increase is at least 2% by volume.

Preference is given in accordance with the invention to regeneration processes according to the invention for which 0.2% by volume ≦ $\Delta G^{max}$ ≦ 4% by volume, preferably 0.2% by volume ≦ $\Delta G^{max}$ ≦ 3% by volume, more preferably 0.2% by volume ≦ $\Delta G^{max}$ ≦ 2% by volume and most preferably 0.3% by volume ≦ $\Delta G^{max}$ ≦ 2% by volume, or 0.4% by volume ≦ $\Delta G^{max}$ ≦ 2% by volume. Another favorable inventive procedure is one with 0.5% by volume ≦ $\Delta G^{max}$ ≦ 2% by volume, or 0.4% by volume ≦ $\Delta G^{max}$ ≦ 1.5% by volume or 0.5% by volume ≦ $\Delta G^{max}$ ≦ 1.5% by volume.

$\Delta G^{max}$ is the highest increase in the content of carbon oxides in the regeneration gas that the regeneration gas experiences in the course of the regenerating flow of the regeneration gas through the catalyst bed in the course of the process according to the invention (i.e. within the period t).

The period t of the process according to the invention can extend over a few minutes to hours (for example ≧1 h, or ≧2 h, or ≧3 h) or else over a few days (for example ≧24 h, or ≧48 h, or ≧72 h). In general, the process according to the invention will not take more than 14 days. It will be appreciated that the process according to the invention can also be interrupted temporarily and then restarted.

In general the process according to the invention will be operated at least until the content of carbon-comprising constituents deposited in the deactivated dehydrogenated catalyst bed is only ≦75% by weight (preferably ≦50% by weight, more preferably ≦25% by weight, better ≦10% by weight, even better ≦5% by weight, or ≦1% by weight and most preferably ≦0.1% by weight, or 0% by weight) of the deposited carbon-comprising constituents present therein at the start of the process (in each case calculated as weight of carbon present in these constituents).

The increase in the regeneration gas content of molecular oxygen required at least three times in accordance with the invention within the period t can be effected, for example, as a single abrupt increase in each case. However, it can also be implemented as a series of smaller abrupt increases and/or else in the form of continuous increase. When an increase of 2% by volume is achieved in the course of a continuous increase in the regeneration gas content of molecular oxygen, the requirement for a single inventive increase in the regeneration gas content of molecular oxygen is thus fulfilled.

Up to the end of the process according to the invention for regeneration (i.e. up to the time t) the oxygen content of the regeneration gas must, in accordance with the invention, thus be increased in total by at least 6% by volume. Preferably in accordance with the invention, the aforementioned (integral) increase is at least 8% by volume, more preferably at least 10% by volume, even more preferably at least 12% by volume and even better at least 14% by volume or at least 16% by volume. Also favorable in accordance with the invention is an aforementioned (integral) total increase in the oxygen content of the regeneration gas of at least 18% by volume, or at least 19% by volume, or at least 20% by volume. In general, the total increase is, though, not more than 21% by volume.

In other words, the oxygen content of the regeneration gas in the process according to the invention in the period t will preferably be increased by at least 2% by volume at least three times or four times, better at least five times or at least seven times, even better at least eight times or at least nine times.

In general, an increase will be undertaken when, under otherwise constant regeneration conditions, ΔG approaches zero (for example goes below the value of 0.01% by volume).

In addition, it is favorable for the process according to the invention when the content of molecular oxygen in the regeneration gas to be conducted through the catalyst bed on commencement (at the start) of the process according to the invention is ≦15% by volume, preferably ≦10% by volume, more preferably ≦5% by volume, even more preferably ≦3% by volume and even better ≦2% by volume or ≦1% by volume. Normally, the content of molecular oxygen in the regeneration gas to be conducted through the catalyst bed on commencement of the process according to the invention will, however, be ≧0.25% by volume, usually ≧0.5% by volume and in many cases ≧0.75% by volume.

Frequently, the content of molecular oxygen in the regeneration gas to be conducted through the catalyst bed will, in the course of the process according to the invention thus vary in the range from 0.25% by volume to 21% by volume.

The temperature of the molecular oxygen comprising regeneration gas on entry thereof into the deactivated catalyst bed when the process according to the invention is performed is, appropriately, from an application point of view, from 200 to 700° C., preferably 300 to 600° C., more preferably 400 to 600° C., even more preferably 420 to 550° C. or from 440 to 470° C.

Advantageously, according to the invention the process according to the invention should be performed in such a way that the temperature of the regeneration gas on exit from the catalyst bed is still below that temperature which, in the course of the heterogeneously catalyzed partial dehydrogenation which the deactivation of the catalyst bed has caused, has occurred as the highest temperature in the catalyst bed (or at least below 1.5 times this temperature). Advantageously, the highest temperature occurring in the catalyst bed in the course of the regeneration process according to the invention is at values of ≦700° C., preferably ≦650° C., more preferably ≦600° C. and most preferably ≦575° C. or ≦550° C.

It has been found to be appropriate in accordance with the invention when the highest temperatures T occurring in the catalyst bed in the course of the regeneration process according to the invention (within the period t), based on the highest temperature $T^{max}$ which occurred in the catalyst bed in the course of the heterogeneously catalyzed partial dehydrogenation which causes the deactivation of the catalyst bed, fulfill the following conditions: $0.5 \cdot T^{max} \leq T \leq 1.5 \cdot T^{max}$, or, $0.5 \cdot T^{max} \leq T \leq 1 \cdot T^{max}$.

Advantageously, the procedure in the regeneration process according to the invention will be to increase the temperature of the molecular oxygen-comprising regeneration gas on entry into the catalyst bed to be regenerated at least once in the course of the dehydrogenation process according to the invention (i.e. within the period t).

The loading of the catalyst bed with regeneration gas or with reaction gas shall be understood in this document to mean the amount of regeneration gas or reaction gas in standard liters (=l (STP); the volume in liters that the appropriate amount of regeneration gas or reaction gas would take up under standard conditions, i.e. at 0° C. and 1 atm) which is conducted through one liter of catalyst bed per hour. In both cases, pure inert material beds are not counted as belonging to the catalyst bed. When the catalyst bed consists of catalyst diluted with pure inert material, this inert material is counted as belonging to the catalyst bed with regard to a calculation of the loading of the catalyst bed with regeneration gas, but not with regard to a calculation of the loading of the catalyst bed with reaction gas. For other requirements of the process according to the invention, both pure inert material beds and inert dilutions are counted as belonging to the catalyst bed.

The loading may also be based only on one constituent of the regeneration gas or only on one constituent of the reaction gas. In that case, it is the amount of this constituent in 1 (STP)/(l·h) (or, for short: l (STP)/l·h, or even shorter: h$^{-1}$), which is conducted through one liter of the catalyst bed per hour.

Advantageously in accordance with the invention, loadings of the catalyst bed with regeneration gas which are ≧500 l (STP)/l·h will be employed in the regeneration process according to the invention. High loadings of the catalyst bed with regeneration gas generally cause an increased proportion of inert gas in the regeneration gas. Such an increased content of inert gas is advantageous in accordance with the invention in that it counteracts elevated carbon oxide concentrations (especially elevated carbon monoxide concentrations) in the regeneration gas. Elevated carbon monoxide contents in the regeneration gas are found to be disadvantageous in accordance with the invention in that it has a markedly chemically reducing action which has an adverse effect on the reactivation of the catalyst bed. Although this is true of carbon dioxide only to a significantly less marked degree, it is capable of reacting with carbon deposits still present to give CO and in this way of forming locally elevated carbon monoxide concentrations, in particular. In addition, the heat capacity of the inert gas fraction promotes the discharge of the heat of reaction formed in the course of the regeneration process.

In general, the loading of the catalyst bed with regeneration gas will, however be ≦50 000 l (STP)/l·h since increasing the loading of the catalyst bed with regeneration gas is accompanied by an increased pressure drop.

Loadings B of the catalyst bed with regeneration gas which are preferred in the process according to the invention are therefore 1000 l (STP)/l·h≦B≦40 000 l (STP)/l·h, more preferably 2000 l (STP)/l·h≦B≦30000 l (STP)/l·h, more preferably 3000 l (STP)/l·h≦B≦20 000 l (STP)/l·h and even more preferably 4000 l (STP)/l·h≦B≦15 000 l (STP)/l·h, or 5000 l (STP)/l·h≦B≦10 000 l (STP)/l·h. At comparatively low contents of carbon-comprising deposits in the deactivated catalyst bed, the loading B will, advantageously and in accordance with the invention, be selected at a lower level (for example from 300 l (STP)/l·h to 700 l (STP)/l·h).

Advantageously in accordance with the invention, the loading B of the catalyst bed with regeneration gas passes through a maximum in the course of the regeneration process according to the invention (within the period t).

In other words, for example, the process according to the invention is commenced initially with moderate loading in order to increase it gradually up to a maximum value in the course of the regeneration process. Proceeding from this, the loading of the catalyst bed with regeneration gas is then lowered again.

Typical starting loadings may, for example, be from 4000 to 8000 l (STP)/l·h. Typical maximum loadings may, for example, be from 7000 to 11 000 l (STP)/l·h. Typical end loadings may, for example be from 500 to 4000 l (STP)/l·h. At comparatively low contents of carbon-comprising deposits in the deactivated catalyst bed, it is possible for aforementioned values also to be, for example, from 400 to 600 l (STP)/l·h (start), from 1000 to 3000 l (STP)/l·h (maximum) and from 500 to 2000 l (STP)/l·h (end).

When air is used as the oxygen source for the molecular oxygen present in the regeneration gas in the process according to the invention, the above-described loading profile of the catalyst bed to be regenerated can be realized in a simple manner, for example, as follows. The regeneration is commenced with a gas mixture stream which is obtained by combining an air stream and a gas stream consisting predominantly (to an extent of more than 50% by volume) of inert gas. Subsequently, the latter is essentially retained and the air stream is gradually increased over the regeneration time (the amount of air fed per unit time). With increasing regeneration time, this simultaneously brings about an increase in the oxygen content in the regeneration gas. When the air stream has reached its maximum value, the reduction in the gas stream consisting predominantly of inert gas is subsequently commenced. On the one hand, this causes a further increase in the oxygen content in the regeneration gas, and, on the other hand, reduces the loading of the catalyst bed with regeneration gas. Advantageously in accordance with the invention, the regeneration gas toward the end of the regeneration process according to the invention consists only of the air stream. Appropriately from an application point of view, this then also has the highest temperature of the regeneration gas employed in the course of the regeneration process when it enters the catalyst bed to be regenerated.

Advantageously, this regeneration gas stream which has the highest oxidation potential will then be retained for a certain time in order to deploy this maximum oxidizing action. This is quite generally advantageous in the process according to the invention. In other words, in general, in the process according to the invention, the process according to the invention will be concluded with that regeneration gas stream which has the highest oxidation potential (i.e. typically the highest content of molecular oxygen and the highest temperature on entry into the catalyst bed) (conversely, the process according to the invention will preferably be commenced with the regeneration gas stream which has the lowest oxidation potential in the course of the process according to the invention).

In this document, an inert gas (for the inventive regeneration or heterogeneously catalyzed partial dehydrogenation) is understood to mean gases other than molecular oxygen and other than hydrocarbons which, as a constituent of regeneration gas or reaction gas in the course of the regenerating or dehydrogenating flow through the fixed catalyst bed, remain chemically unchanged to an extent of at least 95 mol %, preferably to an extent of at least 97 mol % and more preferably to an extent of at least 99 mol % (each constituent of the inert gas taken alone) (under the particular regeneration or dehydrogenation conditions). Examples of inert gases suitable in accordance with the invention (inert diluent gases) are (both for the case of regeneration and the case of heterogeneously catalyzed partial dehydrogenation) $N_2$, He, Ne, Ar and $H_2O$ and, with the restriction already addressed, $CO_2$, and also mixtures of two or more of these gases. An inert gas very particularly preferred in accordance with the invention, especially for the case of the inventive regeneration, is molecular nitrogen.

The aforementioned inert gas definition also applies thus to the reaction gases of other, for example heterogeneously catalyzed, gas phase reactions.

Over long sections of the regeneration process according to the invention, the regeneration gas comprises, appropriately in accordance with the invention, more (or $\geq$) than 78% by volume, frequently even more (or $\geq$) than 80% by volume or more (or $\geq$) than 90% by volume of inert gas (in many cases $N_2$).

At the same time, the regeneration gas in the process according to the invention should be fed to the fixed catalyst bed to be regenerated with elevated temperature. In order to minimize both the requirement for inert gas for this purpose and the requirement for energy for this purpose, the regeneration gas in the process according to the invention will, advantageously in accordance with the invention, be circulated at least partly and be reused as a constituent of regeneration gas to be conducted freshly through the catalyst bed.

In other words, the regeneration gas exiting from the catalyst bed to be regenerated is (at least partly) frequently for the most part (in principle, the recycled regeneration gas fraction, based on the regeneration gas volume flow rate exiting from the catalyst bed, may be, for example, from 10 to 97% by volume (or from 10 to 95% by volume or from 10 to 90% by volume) or from 30 to 60% by volume) be recycled to the reactor inlet and supplemented with sufficient gas used as the oxygen source (for example air or pure molecular oxygen or a mixture of the two) that the resulting mixture has the content of molecular oxygen desired for the regeneration gas. A volume of regeneration gas exiting from the catalyst bed essentially corresponding to this supplementary amount can be removed before the recycling of the regeneration gas and disposed of (for example combustion in a flare or in a burner for the purposes of energy generation). When a reduction in the loading of the catalyst bed to be regenerated with regeneration gas is desired, the proportion of regeneration gas removed before its recycling will correspondingly be selected at an increasingly greater level.

For the purpose of recycling the regeneration gas to the catalyst bed inlet, a fan (preferably a radial fan) is normally sufficient in order to balance out again the pressure drop suffered in the course of passage through the catalyst bed. In the case of catalyst beds which cause a particularly high pressure drop, the recompression can also be undertaken with the aid of a radial compressor. The oxygen source additionally required to obtain the new regeneration gas is generally available from other sources with the required pressure. If appropriate, it is, though, also compressed actually in a mixture with regeneration gas to be recycled.

Appropriately from an application point of view, the regeneration gas which exits from the catalyst bed to be regenerated and normally has an elevated temperature will be conducted through an appropriate heat exchanger in indirect heat exchange with the regeneration gas to be fed to the catalyst bed to be regenerated. As this occurs, the former cools and the latter is heated to the desired entrance temperature. Typically, the indirect heat exchange is effected before the recompression. In the case that water is condensed out in the course of the cooling, it will, advantageously from an application point of view, be separated out with the aid of droplet separators and conducted out of the regeneration circuit.

Such a water condensation can also result when the regeneration gas to be recompressed, for the avoidance of excessively high temperatures, is additionally cooled, for example, in an air cooler or in a heat exchanger cooled with surface water in the course of the compression. Water condensed out in this way would also be removed, appropriately in accordance with the invention, before a recompression.

Of course, the content of molecular oxygen in the regeneration gas to be conducted through the catalyst bed may also be selected above the content of molecular oxygen in air in the course of the regeneration process according to the invention.

For example, it would also be possible to use pure molecular oxygen as the regeneration gas toward the end of the regeneration process according to the invention. For reasons of economic viability, the content of molecular oxygen in the regeneration gas to be conducted through the catalyst bed will normally not exceed that of air.

Advantageously in accordance with the invention, the CO content of the regeneration gas to be conducted through the catalyst bed, even in the above-described cycle gas method, on entry of the regeneration gas into the catalyst bed, will be $\leqq 3\%$ by volume, preferably $\leqq 2\%$ by volume, more preferably $\leqq 1\%$ by volume, and most preferably $\leqq 0.1\%$ by volume or $\leqq 0.05\%$ by volume. This is not least because elevated CO concentrations in the regeneration gas appear to act against the inventive objectives in an exceptional manner.

Quite generally, the content of the constituents other than inert gas, carbon oxides and molecular oxygen in the regeneration gas when it enters the catalyst bed is, advantageously in accordance with the invention, $\leqq 2\%$ by volume, better $\leqq 1\%$ by volume, preferably $\leqq 0.5\%$ by volume, even more preferably $\leqq 0.1\%$ by volume and at best 0% by volume.

In principle, the regeneration gas can be sucked through the catalyst bed to be regenerated in the process according to the invention. In this case, the working pressure in the regeneration process according to the invention is below atmospheric pressure. Preference is given in accordance with the invention to working pressures in the course of the regeneration process according to the invention which are from 1 to 10 bar, preferably from 1 to 6 bar, and more preferably from 1.5 to 4 bar above atmospheric pressure. The reason for this is not least because working at superatmospheric working pressures advantageously enables elevated partial $O_2$ pressures.

The process according to the invention is suitable both in the case of deactivated catalyst beds which are accommodated in (in the reaction chamber of) adiabatic, i.e. adiabatically configured (with reaction chambers thermally insulated from their external environment), reactors and in the case of deactivated catalyst beds which are accommodated in isothermal, i.e. isothermically configured, reactors (enable control of the temperature in the reaction chamber by heat exchange with heat carriers conducted outside the reaction chamber) (in each case the catalyst bed is present in the reaction chamber).

At this point, it should be emphasized that, in the regeneration process according to the invention, the temperature in the catalyst bed preferably essentially does not fall below the entrance temperature of the regeneration gas into the catalyst bed as the regeneration gas passes through the catalyst bed to be regenerated. In the case of a catalyst bed to be regenerated which is disposed in an adiabatic reactor, this prerequisite is normally largely satisfied by virtue of the adiabaticity of the reactor. In the case of a catalyst bed disposed in an isothermal reactor, the temperature of the external heat carrier medium has to be adjusted correspondingly.

Conversely, the difference between the temperature of the regeneration gas on entry into the catalyst bed $T^E$, and the temperature of the same regeneration gas on exit from the catalyst bed, $T^A$, i.e. $T^A - T^E$, in the process according to the invention should, especially in the case of catalyst beds to be reactivated which are disposed in adiabatic reactors, be $\leqq 250°$ C., better $\leqq 150°$ C., preferably $\leqq 100°$ C. A $T^A - T^E$ difference favorable in accordance with the invention is about 50° C.

In principle, the catalyst bed in the process according to the invention may be either a fixed catalyst bed or a fluidized catalyst bed. Preferably in accordance with the invention, the catalyst bed to be regenerated in accordance with the invention is a fixed catalyst bed (all statements in this patent application therefore apply in particular in the case of a fixed catalyst bed). The inventive procedure is of particular relevance when the bed volume of the fixed catalyst bed is $\geqq 50$ l and $\leqq 10\,000$ m$^3$, generally $\leqq 5000$ m$^3$ and usually $\leqq 1000$ m$^3$ or $\leqq 500$ m$^3$ or $\leqq 50$ m$^3$. This is true especially when the fixed catalyst bed is disposed in an adiabatic reactor or its reaction chamber. This is caused not least by the fact that the heat capacity of the reactor material loses an increasing amount of importance and influence with increasing bed volume of the fixed catalyst bed.

The necessity of performing a partial dehydrogenation of a hydrocarbon to be dehydrogenated over dehydrogenation catalysts having selective action in the solid state is caused by the fact that the dehydrogenation (cleavage of C—H) competes kinetically with thermal cleavage or cracking (cleavage of C—C).

Owing to the selective catalysts, in the case of a heterogeneously catalyzed dehydrogenation of a hydrocarbon to be dehydrogenated (e.g. propane), the dehydrogenated hydrocarbon (e.g. propylene) is formed with increased selectivity. In that case, by-products, for example methane, ethylene and ethane are formed only in comparatively minor amounts.

The regeneration process according to the invention can be employed for all dehydrogenation catalysts known in the prior art.

For the case of heterogeneously catalyzed dehydrogenations other than heterogeneously catalyzed oxydehydrogenations, these known dehydrogenation catalysts can be divided roughly into two groups, specifically into those which are oxidic in nature (for example chromium oxide and/or aluminum oxide) and into those which consist of at least one metal deposited (in an elemental form) on a generally oxidic (for example zirconium dioxide, aluminum oxide, silicon dioxide, titanium dioxide, magnesium oxide, lanthanum oxide and/or cerium oxide) support. In general, at least one of the deposited metals is a comparatively noble metal (for example an element from the group comprising Cu, Ag, Au, Zn, Cd, Hg and the elements of the third transition group (e.g. Ru, Rh, Pd, Os, Ir, Pt), or an element from the platinum group, for example platinum and/or palladium). The aforementioned catalysts thus include, for example, those which comprise, on the (generally oxidic) catalyst support, one or more elements selected from the group consisting of elements of transition group VIII and/or VI, and if appropriate, one or more further elements selected from the group consisting of elements of main group I and II, transition group III including the lanthanides, main group III, rhenium, zinc and tin.

Suitable dehydrogenation-active elements are in particular metals of transition group VIII, preferably the noble metals platinum and palladium, more preferably platinum. When a noble metal is used as the dehydrogenation-active element, additional metals which slow the sintering of the noble metal, such as Re and/or Sn, may be present. Possible further elements include those which are known to influence the acidity of the catalyst surface or can stabilize noble metals against sintering. Such further elements are elements of main group I and II, specifically Li, Na, K, Rb, Cs, Mg, Ca, Sr and Ba and also elements of transition group III, especially Y and La, including the lanthanides. Zn has also been found to be effective. Instead of a noble metal (or in addition to it), it is also possible for dehydrogenation-active metals of transition group VI, especially chromium or molybdenum, to be present on the catalyst support. For the needs of this document, the two aforementioned groups shall be differentiated from one another as "oxidic dehydrogenation catalysts" and as "metallic dehydrogenation catalysts". The regeneration process according to the invention is thus applicable to all dehydrogenation catalysts which are disclosed in DE-A 10 2006 035 718, WO 01/96270, DE-A 10219879, EP-A 731 077, DE-A 10131297, WO 99/46039, U.S. Pat. No. 4,788,371, EP-A 705 136, WO 99/29420, U.S. Pat. No. 4,220,091, U.S. Pat. No. 5,430,220, U.S. Pat. No. 5,877,369, EP-A 117 146, DE-A 19937196, DE-A 19937105, U.S. Pat. No. 3,670,044, U.S. Pat. No. 6,566,573, WO 01/83405 and WO 94/29021 and also the prior art cited in these documents. This is true especially when these dehydrogenation catalysts have been deactivated in the course of the heterogeneously catalyzed dehydrogenations, described in these documents, of hydrocarbons to be dehydrogenated.

In contrast to the above, useful catalysts for heterogeneously catalyzed oxydehydrogenations are essentially exclusively catalysts which are of oxidic nature (for example those based on MoVNb oxides, or based on vanadyl pyrophosphate (they may additionally comprise promoters).

The regeneration process according to the invention is thus additionally suitable for all oxydehydrogenation catalysts which are disclosed in the documents U.S. Pat. No. 4,788,371, CN-A 1073893, Catalysis Letters 23 (1994), 103-106, W. Zhang, Gaodeng Xuexiao Huaxue Xuebao, 14 (1993) 566, Z. Huang, Shiyon Huagong, 21 (1992) 592, WO 97/36849, DE-A 19753817, U.S. Pat. No. 3,862,256, U.S. Pat. No. 3,887,631, DE-A 19530454, U.S. Pat. No. 4,341,664, J. of Catalysis 167, 560-569 (1997), J. of Catalysis 167, 550-559 (1997), Topics in Catalysis 3 (1996) 265-275, U.S. Pat. No. 5,086,032, Catalysis Letters 10 (1991), 181-192, Ind. Eng. Chem. Res. 1996, 35, 14-18, U.S. Pat. No. 4,255,284, Applied Catalysis A: General, 100 (1993), 111-130, J. of Catalysis 148, 56-67 (1994), V. Cortes Corberan and S. Vic Bellón (Ed.), New Developments in Selective Oxidation II, 1994, Elsevier Science B.V., S. 305-313, $3^{rd}$ World Congress on Oxidation Catalysis, R. K. Grasselli, S. T. Oyama, A. M. Gaffney and J. E. Lyons (Ed.), 1997, Elsevier Science B.V., S. 375 ff or in DE-A 19837520, DE-A 19837517, DE-A 19837519, DE-A 19837518, EP-A 938463, EP-A 167 109, DE-A 19838312 and DE-A 19753817. This is especially true when these oxydehydrogenation catalysts have been deactivated in the course of the heterogeneously catalyzed oxydehydrogenations, described in these documents, of hydrocarbons to be dehydrogenated.

Including the oxidic oxydehydrogenation catalysts, the overall variety of known dehydrogenation catalysts can thus be divided overall into "oxidic dehydrogenation catalysts" and into "metallic dehydrogenation catalysts".

In the case of the oxidic dehydrogenation catalysts, the inventive regeneration will generally be ended when $\Delta G$, in the course of passage of the regeneration gas with the highest oxidation potential (i.e. with the highest contemplated entrance temperature of the regeneration gas into the catalyst bed and with the highest contemplated content of molecular oxygen in the regeneration gas) through the catalyst bed to be regenerated, tends essentially toward zero. In order to have increased reliability regarding this point in time, it is appropriate from an application point of view to lower the working pressure from time to time as the regeneration gas with the highest oxidation potential passes through the catalyst bed (for example from 3.5 bar of superatmospheric pressure to 0 bar of superatmospheric pressure), in order thus to ease outgassing of any catalyst pores still filled with carbon oxides. This can be effected in a simple manner by means of a pressure-retaining valve at the outlet from the reactor, which is, in a simple manner, appropriately opened further for this purpose or increasingly closed again to reestablish the working pressure.

When an essentially vanishing $\Delta G$ is attained (to check, the oxidation potential of the regeneration gas can be increased slightly and it can be checked whether $\Delta G$ remains unchanged), the dehydrogenation catalyst has essentially been freed again of the carbon-comprising deposits. The elemental constituents are present again in the reoxidized state and the dehydrogenation catalyst, in the case of an oxidic dehydrogenation catalyst, is again ready for use for the purpose of the heterogeneously catalyzed dehydrogenation. In other words, the entrance temperature of the regeneration gas with the highest selected oxidation potential will finally be adjusted to the value which corresponds to the entrance temperature of the reaction gas for the heterogeneously catalyzed dehydrogenation started up again after the regeneration, and then the regeneration gas stream will be shut down and replaced by the corresponding reaction gas stream.

Of course, the inventive regeneration can also be ended actually before $\Delta G$ has essentially attained the value of zero. In this case, although the regeneration does not reach its maximum possible extent, use is nevertheless made of the advantageousness of the inventive procedure. Especially from the point of view of a consideration of the overall economic viability, it may be appropriate in accordance with the invention to end the inventive regeneration actually before $\Delta G$ has essentially attained the value of zero, and to resume the heterogeneously catalyzed dehydrogenation early. In the interplay of time consumed and dehydrogenation performance, the economic optimum may quite possibly be at a partial regeneration (the position of the economic optimum has to be determined for the particular catalyst system by means of a few individual experiments).

When the dehydrogenation catalyst used is, in contrast, a metallic dehydrogenation catalyst, the so-called redispersion begins to become complete when an essentially vanishing $\Delta G$ has been attained with the regeneration gas having the highest oxidation potential.

As already mentioned, the metallic catalysts are those catalysts which consist of at least one metal deposited on a generally oxidic support. For a high activity of such a catalyst, it is advantageous when the metallic phase is distributed in very fine dispersion on the support surface. For this purpose, in the preparation of such a catalyst, an oxidized form of the particular metal will normally initially be deposited on the support (for example in the form of a salt solution of the appropriate metal, by appropriate impregnation of the support with the salt solution). Owing to the attractive interaction between metal salt and for example, oxidic support, the metal, on completion of impregnation, is distributed particularly uniformly on the outer and inner support surface. Subsequently, the metal applied in ionic form is typically converted to its elemental form by chemical reduction without the degree of spread of the metal on the support achieved before the reduction being significantly impaired. Normally two phenomena contribute to the deactivation of a metallic dehydrogenation catalyst in the course of the long-term operation of a heterogeneously catalyzed partial dehydrogenation: firstly, the deposition of carbons and/or high-boiling hydrocarbons already described, and secondly a loss of the degree of spread of the dispersed metal distribution on the support which accompanies long-term operation. The latter is presumably attributable to the fact that the metal-metal interaction exceeds the metal-support interaction in elemental form, which is why the original degree of spread degenerates in the course of the long-term operation of a heterogeneously catalyzed dehydrogenation.

In the regeneration process according to the invention, there is thus not only an elimination of the carbon-comprising deposits mentioned. Instead, at least a portion of the metal which causes the catalytic dehydrogenating action is also converted to an oxidic form. In the oxidic form, though, an increased interaction with the support again arises, which results in a desired redispersion. When, therefore, in the process according to the invention, even when a ΔG of essentially zero has been attained, regeneration gas with the highest oxidation potential is still allowed to act in the inventive manner on the deactivated metal catalyst, this promotes the above-described redispersion. Reference is therefore also made to the redispersion phase within the inventive regeneration process in the case of its application to deactivated metallic dehydrogenation catalysts. With increasing redispersion time, the desired redispersion generally increases. In a typical manner from an application point of view, the redispersion phase will normally take a period of a few hours (e.g. $\geq 2$ h, or $\geq 6$ h) up to a few days (e.g. $\leq 5$ days). The quality of redispersion achieved in each case has to be checked experimentally in each individual case by means of sampling, by using the catalyst sample again as a dehydrogenation catalyst. At this point, it should be emphasized that the regeneration gas during the redispersion phase, advantageously in accordance with the invention, does not comprise any steam. In contrast, in the reactivation of deactivated oxidic dehydrogenation catalysts, presence of steam in the regeneration gas generally has an advantageous effect over the overall inventive regeneration zone. In the case of deactivated metallic catalysts, this generally also applies to the regeneration phase preceding the redispersion phase.

However, such steam contents of the regeneration gas should generally not exceed 20% by volume. Normally, such steam contents should, however, be $\geq 1\%$ by volume.

At the same time, it should be taken into account that the oxidation of high-boiling hydrocarbons deposited on the deactivated dehydrogenation catalyst as an oxidation product also forms water.

The metallic dehydrogenation catalyst which has been reoxidized in accordance with the invention and generally additionally redispersed is, however, in contrast to the oxidic dehydrogenation catalyst reoxidized in accordance with the invention, not immediately suitable as such for the catalysis of heterogeneously catalyzed partial dehydrogenations of hydrocarbons to be dehydrogenated.

Instead, this also requires, after the inventive regeneration, a further reduction of the metallic constituents of the redispersed metallic dehydrogenation catalyst in their elemental state. Advantageously, from the application point of view, molecular hydrogen is used for this purpose. For this purpose, it is passed through the catalyst bed at elevated temperature either as such or in inert gas-diluted form. The hydrogen content of such a reducing gas should be $\geq 1\%$ by volume, preferably $\geq 3\%$ by volume and more preferably $\geq 5\%$ by volume.

Advantageously in accordance with the invention, such reducing gases used should be gas mixtures which comprise at least 40% by volume (preferably from 40 to 60% by volume) of molecular hydrogen and, as the remainder, essentially inert gas. Suitable inert gas constituents of the reducing gas are in particular Ar, He, Ne, $N_2$ and $H_2O$. Appropriately from an application point of view, the inert gas used in the reducing gas is molecular nitrogen and/or steam. The sole use of molecular nitrogen is preferred. Frequently, however, reducing gases are used which, as well as nitrogen, comprise up to 5% by volume, or up to 3% by volume, or up to 1% by volume, of steam as an inert diluent gas. This is the case not least when the reducing gas, as already indicated for the inventive regeneration gas, is circulated. Such a cycle method is appropriate in particular because the reducing gas has the molecular hydrogen as a reducing agent, compared to the oxide content of the redispersed metallic dehydrogenation catalyst, in a considerable excess relative to the reaction stoichiometry (metal oxide+$H_2 \rightarrow H_2O$+metal) (the oxidic supports are normally hard-fired (calcined at high temperature) and are normally not attacked by the reducing atmosphere). The shaped inert bodies for diluting the catalyst bed are typically manufactured from corresponding hard-fired oxidic materials. Their specific pore volume is generally $\leq 0.5$ cm$^3$/g (preferably $\leq 0.25$ cm$^3$/g) and their specific surface area $\leq 100$ cm$^2$/g, preferably $\leq 70$ cm$^2$/g.

In addition, a cycle gas method in this case too ensures the retention of the heat content of the reducing gas. Frequently, it is not even necessary to supplement fresh molecular hydrogen into the circulated reducing gas.

The theme of retention of the heat content is relevant not least because the reduction to the elemental metal likewise requires elevated temperatures. The exothermicity accompanying the reduction itself is comparatively minor ("only slightly exothermic").

In general, the temperature of the reducing gas (of the gas with reducing action) on entry into the catalyst bed will be from 350 to 600° C., preferably from 400 to 550° C., or from 400 to 500° C. More preferably, the aforementioned entrance temperature is from 430 to 480° C. The above is true especially in the case of a deactivated catalyst bed disposed in an adiabatic reactor.

Excessively high temperatures in the catalyst bed should be avoided in the course of the aforementioned reduction, since they may counteract the redispersion brought about in the course of the inventive regeneration.

Just like the regeneration gas, the reducing gas may also in principle be sucked through the catalyst bed. In this case, the working pressure in the reducing operation will generally be below standard pressure. However, this working pressure is preferably also above atmospheric pressure in the reducing operation, when the reducing gas is also forced through the catalyst bed. Typical working pressures in the inventive reducing operation vary from 1 to 10 bar, preferably from 1 to 6 bar and more preferably from 1 to 3 bar above atmospheric pressure.

Otherwise, the statements made for the cycle gas mode of the inventive regeneration gas apply to the cycle gas mode of the reducing gas. The reducing operation will be ended essentially when the content of steam in the reducing gas (expressed in % by volume) on exit from the catalyst bed, in comparison to the same content on entry of the reducing gas into the redispersed catalyst bed, is essentially no longer increased.

To complete the reduction, the temperature of the reducing gas on entry thereof into the catalyst bed will be adjusted to the value which corresponds to that temperature that the reaction gas will have when the dehydrogenation process is restarted after the regeneration of the deactivated metallic dehydrogenation catalyst has ended. This preheats the catalyst bed to this temperature. Subsequently, the supply is switched from reducing gas to reaction gas.

At this point, it should be emphasized once again that all statements made in this document apply especially when the catalyst bed is a fixed catalyst bed and in particular when the catalyst bed (the fixed catalyst bed) is present in an adiabatic reactor. The aforementioned is true in particular when the deactivation is effected in the course of a heterogeneously catalyzed dehydrogenation (for example one of propane to propylene) other than a heterogeneously catalyzed oxydehydrogenation.

In this document, an inert gas shall be understood to mean a gas which consists to an extent of ≧98.5% by volume of the inert gas. In other words, when molecular nitrogen is also used as an inert gas, it is possible for this purpose in principle to use industrial nitrogen with a purity of ≧98.5% by volume (i.e., nitrogen which may still comprise up to 1.5% by volume of molecular oxygen). The constituents other than nitrogen (the inert component) and other than molecular oxygen should, however, in their entirety be limited to ≦0.5% by volume.

Preference will of course be given in accordance with the invention to inert gas with purities of ≧99% by volume, preferably ≧99.5% by volume and more preferably ≧99.9% by volume.

In general, a deactivated dehydrogenation catalyst bed to be regenerated in accordance with the invention will, based on its weight (not including pure inert material beds) have from 0.5 or 1 to 10% by weight of constituents comprising carbon deposited therein (expressed as proportion by weight of the elemental carbon present therein). Especially when a metallic dehydrogenation catalyst is used and the reaction gas mixture used for the heterogeneously catalyzed partial dehydrogenation comprises added external molecular hydrogen and generally steam, the loss of the degree of metallic spread may even already cause a significant deactivation of the catalyst even without exorbitant coking (the effect of the lower degree of spread can dominate the effect of coking).

Otherwise, it has been found to be appropriate, before the startup of the regeneration process according to the invention and after the interruption of the heterogeneously catalyzed dehydrogenation which leads to the deactivation of the catalyst bed, to initially flush the catalyst bed with inert gas (for example $N_2$, $H_2O$ and/or noble gases). This achieves the effect that, firstly, the catalyst bed, before the commencement of the inventive regeneration, is freed of reactants and products which are still present in the catalyst bed and may disrupt the regeneration process according to the invention. Secondly, with suitable selection of the entrance temperature of the flushing gas into the deactivated catalyst bed, the temperature thereof, which is of course elevated at the end of a dehydrogenation cycle, can be reduced to a value which is more compatible with an advantageous inventive regeneration (for example from over 550° C. to below 450° C.). The temperature of the flushing gas used for this purpose will, on entry into the (fixed) catalyst bed, generally be in the range from ≧25° C. to ≦100° C. It will be appreciated that the flushing gas may also be fed to the catalyst bed heated to a temperature above these temperatures. This procedure will generally be selected when the (fixed) catalyst bed is not be cooled too rapidly in order to avoid the occurrence of thermal stresses in the dehydrogenation reactor. A particularly favorable flushing gas has been found to be a mixture of molecular nitrogen and steam which comprises up to 5% by volume of steam.

Even in the case of flushing of the catalyst bed with flushing gas, it is generally appropriate to circulate at least some of the flushing gas. This is true especially when all reactants and products which may disrupt the regeneration process according to the invention have already been flushed out of the catalyst bed, but the temperature of the catalyst bed has not yet been lowered to a temperature compatible with the advantageous inventive regeneration. In order to limit the demand for fresh flushing gas, the heated flushing gas flowing out of the catalyst bed will, in this case, appropriately, from an application point of view, initially be conducted through an indirect heat exchanger (for example an air cooler), in order initially to lower its temperature to the desired temperature, and it will then be recycled into the catalyst bed.

As already mentioned, it is advantageous in accordance with the invention when the loading of the catalyst bed with regeneration gas passes through a maximum in the course of the regeneration process according to the invention. When the cycle gas mode of the regeneration gas discussed is used, this means that increasingly large amounts of regeneration gas have to be circulated at the start of the regeneration process according to the invention, whereas the amount of regeneration gas that has to be circulated toward the end of the regeneration process according to the invention is only comparatively small. In other words, for efficient performance of the process according to the invention, a radial fan is thus required which is capable of delivering either large or small amounts of cycle gas. For this purpose, advantageous radial fans from an application point of view have been found to be those which have two different drive motors with different power (one large, high-performance and one small, lower-performance). The other of the two in each case runs idle. Alternatively, it is also possible to use a drive motor with frequency converter.

Since the catalyst bed, preferably in accordance with the invention, is a fixed catalyst bed, a dehydrogenation catalyst in this document shall be understood to mean in particular a shaped body whose longest dimension L (longest direct line connecting two points on the surface of the shaped body) is from 0.1 or 1 to 100 mm, often from 0.5 to 80 mm or from 0.5 to 50 mm, preferably from 1 to 30 mm or from 2 to 20 mm and more preferably from 2 to 10 mm or from 2 to 5 mm (the above is also true for the longest dimension of shaped inert bodies, with which shaped catalyst bodies can be diluted in the fixed catalyst bed). In the case of dehydrogenation catalysts to be used for heterogeneously catalyzed dehydrogenations other than heterogeneously catalyzed oxydehydrogenations of hydrocarbons to be dehydrogenated, the process according to the invention is applicable especially to those which, in the experiment described below, based on single pass of the reaction gas mixture through the reaction tube, dehydrogenates at least 5 mol % of the propane present in the reaction gas to propylene.

A reaction tube made of steel of EN materials number 1.4835 with a wall thickness of 2 mm and an internal diameter of 35 mm and a length of 80 cm is filled as follows:

50 ml of a bed of the appropriate dehydrogenation catalyst are placed centrally in the reaction tube. Above and below the bed of shaped catalyst bodies, the reaction tube is filled up in each case with a bed of steatite spheres (inert spheres) having a sphere diameter of from 1.5 to 2.5 mm. A grid bears the entire bed. From the outside, the reaction tube is kept at a temperature of 550° C. over its entire length. The reaction tube is charged with a mixture of propane and steam in a volume ratio of 2 (propane) to 1 (steam) with a propane loading of the bed of shaped catalyst bodies of 1000 l (STP)/ l·h. The reaction gas mixture stream conducted into the reaction tube is preheated to a temperature of 550° C. In particular, the process according to the invention is suitable for those dehydrogenation catalysts for which, under the above boundary conditions, the cumulative selectivity of formation of the ethane, ethylene and methane by-products is ≦5 mol %, based on propane converted.

These dehydrogenation catalysts include, for example, those of German application No. 102005044916, but in particular the metallic dehydrogenation catalysts of DE-A 19937170, especially those according to example 1, example 2, example 3 and example 4 of this document.

These are metallic dehydrogenation catalysts which comprise from 10 to 99.9% by weight of zirconium dioxide and from 0 to 60% by weight of aluminum oxide, silicon dioxide and/or titanium dioxide as the support material, and, in elemental form and in a total amount of from 0.1 to 10% by weight, at least one element from the amount comprising the first and the second main group and the elements of the third transition group other than lanthanum, at least one element of the eighth transition group (in each case of the periodic table of the elements) and lanthanum and/or tin, with the proviso that the sum of the percentages by weight is 100% by weight.

These metallic dehydrogenation catalysts also include, as preferred embodiments, those which comprise from 10 to 99.9% by weight of zirconium dioxide and from 0 to 60% by weight of aluminum oxide, silicon dioxide and/or titanium dioxide as the support material, and, in elemental form and in a total amount of from 0.1% to 10% by weight, at least one element of transition group VIII, at least one element of main group I and II, at least one element of main group III and/or IV and at least one element of transition group III including lanthanides and actinides, with the proviso that the sum of the percentages by weight is 100% by weight.

As an element of transition group VIII, the active composition of the aforementioned metallic dehydrogenation catalysts preferably comprises platinum and/or palladium, more preferably platinum. As an element of main group I and II, the active composition of the aforementioned dehydrogenation catalysts preferably comprises potassium and/or cesium. As an element of transition group III including the lanthanides and actinides, the active composition of the aforementioned dehydrogenation catalysts preferably comprises lanthanum and/or cerium. As an element of main group III and/or IV the active composition of the aforementioned dehydrogenation catalysts preferably comprises one or more elements from the group consisting of boron, gallium, silicon, germanium, indium, tin and lead, more preferably tin.

In principle, with regard to the applicability of the inventive procedure to a deactivated fixed catalyst bed, there are no restrictions of any kind with regard to the catalyst geometry (especially in the case of supported catalysts) or with regard to the geometry of any inert shaped bodies used additionally to dilute the fixed catalyst bed. Particularly frequently used geometries are, for example, solid cylinders, hollow cylinders (rings), spheres, cones, pyramids and cubes, and also extrudates, wagon wheels, stars and monoliths.

Especially in the case of heterogeneously catalyzed partial dehydrogenations other than heterogeneously catalyzed partial oxydehydrogenations (in this document, these are the nonoxidative and the oxidative conventional heterogeneously catalyzed partial dehydrogenations), useful geometries for a fixed catalyst bed are: catalyst extrudates (diameter typically from 0.1 or 1 to 10 mm, preferably from 1.5 to 5 mm; length typically from 1 to 20 mm, preferably from 3 to 10 mm); tablets (preferably the same dimensions as for the extrudates) and/or catalyst rings (external diameter and length in each case typically from 2 to 30 mm or to 10 mm, wall thickness appropriately from 1 to 10 mm, or to 5 mm, or to 3 mm). These geometries are in principle also useful as geometries for any shaped inner bodies additionally used to dilute the fixed catalyst bed.

In general, the dehydrogenation catalysts (especially the metallic dehydrogenation catalysts and, among these, especially those recommended in DE-A 19937107 (especially the exemplary catalysts of this DE-A)), which are suitable for oxidative and nonoxidative conventional heterogeneously catalyzed partial dehydrogenations are such that they are capable of catalyzing both the dehydrogenation of the hydrocarbon to be dehydrogenated (e.g. propane) and the combustion of the hydrocarbon to be dehydrogenated (e.g. propane) and the combustion of molecular hydrogen. In the case of a competition situation over the catalysts, the combustion of hydrogen proceeds very much more rapidly both in comparison to the dehydrogenation of the hydrocarbon to be dehydrogenated (e.g. propane) and in comparison to its combustion.

For the performance of a conventional (oxidative or nonoxidative) heterogeneously catalyzed partial dehydrogenation of a hydrocarbon to be dehydrogenated (e.g. propane) which causes the deactivation of the catalyst bed to be regenerated in accordance with the invention and precedes the inventive regeneration, useful reactor types and process variants are in principle all of those known in the prior art.

Descriptions of such process variants are present, for example, in all prior art documents cited in this document with regard to the dehydrogenation catalysts suitable for such dehydrogenations, and also the prior art cited at the outset of this document, and documents DE-A 10 2006 029 790, DE-A 10 2006 035 718, DE-A 10 2006 0017 623, DE-A 10 2006 015 235 and DE-A 10 2005 061 626. The same applies to the documents EP-A 1109763, U.S. Pat. No. 3,308,181, U.S. Pat. No. 3,670,044, U.S. Pat. No. 4,886,928, U.S. Pat. No. 6,566,573, U.S. Pat. No. 4,788,371 and WO 94/29021, and also the prior art cited in these documents.

A comparatively comprehensive description of such conventional heterogeneously catalyzed partial dehydrogenations (nonoxidative or oxidative) is present, for example in Catalytica® Studies Division, Oxidative Dehydrogenation and Alternative Dehydrogenation Processes, Study Number 41920D, 1993, 430 Ferguson Drive, Mountain View, Calif., 94043-5272, U.S.A.

What is characteristic of a conventional partial heterogeneously catalyzed dehydrogenation of hydrocarbons to be dehydrogenated (e.g. propane) is (as already stated), that the dehydrogenation step proceeds endothermically. This means that the heat (energy) required for the establishment of the required reaction temperature has to be supplied either to the reaction gas beforehand and/or in the course of the heterogeneously catalyzed dehydrogenation.

In other words, based on single pass of the reaction gas mixture comprising the hydrocarbon to be dehydrogenated through the catalyst bed, the reaction chamber comprising the catalyst bed can be configured isothermally by controlled heat exchange with, for example fluid (i.e. liquid or gaseous) heat carriers conducted outside the reaction chamber enclosed by a shell (externally controlled temperature profile). Corresponding heat exchangers may, though, also be accommodated in the reaction chamber itself.

A conventional partial heterogeneously catalyzed dehydrogenation of hydrocarbons to be dehydrogenated (e.g. propane) may, with the same reference basis, also be performed adiabatically, i.e. essentially without such a controlled heat exchange with (externally) conducted heat carriers (externally uncontrolled temperature profile). In the latter case, the gross exothermicity based on single pass through the catalyst bed present in the reaction chamber as a result of the internally controlled (for example, by hydrogen combustion in a subsequent step) temperature profile yet to be described below may be configured endothermically (negative) or autothermally (essentially zero) or exothermically (positive).

Typically a conventional heterogeneously catalyzed partial dehydrogenation of at least one hydrocarbon to be dehydrogenated (e.g. of propane), as already mentioned, requires comparatively high reaction temperatures. The achievable conversion is normally limited by the thermodynamic equilibrium. Typical reaction temperatures are from 300 to 800° C., or from 400 to 700° C. One molecule of hydrogen is obtained per molecule of, for example, propane dehydrogenated to propylene. High temperatures and removal of the reaction product $H_2$ shift the equilibrium position toward the target product, as does lowering the partial pressure by inert dilution. The accompanying working pressures are generally from 0.2 to 10 bar, or from 0.5 to 6 bar or from 0.5 to 3 bar (in each case, absolute).

It is also, as already stated, typical of conventional heterogeneously catalyzed partial dehydrogenations of at least one hydrocarbon to be dehydrogenated (e.g. of propane), owing to the high reaction temperatures required, that high-boiling high molecular weight organic compounds, up to and including carbon, are formed in certain amounts, are deposited on the catalyst surface and thus deactivate it. In order to minimize this disadvantageous accompanying phenomenon, the reaction gas which comprises the hydrocarbon to be dehydrogenated (e.g. the propane) and is to be passed over the catalyst surface at elevated temperature for the conventional heterogeneously catalyzed dehydrogenation can be diluted with steam. Carbon which is deposited is continuously partly eliminated again under the resulting conditions by the principle of coal gasification.

A certain suppression of the formation of carbon deposits (and hence a prolonging of the catalyst lifetime (operating time of a heterogeneously catalyzed partial dehydrogenation between two regenerations of the catalyst bed)) is also possible by adding molecular hydrogen to the hydrocarbon to be dehydrogenated conventionally under heterogeneous catalysis (e.g. propane) before it is conducted over the dehydrogenation catalyst at elevated temperature.

It will be appreciated that the possibility also exists of adding steam and molecular hydrogen in a mixture to the hydrocarbon to be dehydrogenated conventionally under heterogeneous catalysis (e.g. propane), especially for the above purposes. Addition of molecular hydrogen to the conventional heterogeneously catalyzed dehydrogenation of propane also reduces the undesired formation of allene (propadiene), propine and acetylene as by-products.

It may (as already addressed) be appropriate to perform the conventional heterogeneously catalyzed hydrocarbon (e.g. propane) dehydrogenation (quasi-)adiabatically (for example with comparatively low propane (or generally hydrocarbon) conversion). This means that the reaction gas mixture to be fed to the dehydrogenation (also referred to in this document as starting gas or starting gas mixture) will generally be heated initially to a temperature of from 400 or 500 to 700° C. (or from 550 to 650° C.) (for example by direct firing of the walls surrounding it). Normally, a single adiabatic pass through at least one catalyst bed disposed in the adiabatic reaction chamber will be sufficient to achieve the desired conversion, in the course of which the reaction gas will cool by from about 30° C. to 200° C. (depending on the conversion and dilution). Presence of steam as a heat carrier also manifests itself advantageously from the point of view of an adiabatic method. The comparatively low reaction temperature enables longer lifetimes of the catalyst bed used.

In principle, a conventional heterogeneously catalyzed hydrocarbon (e.g. propane) dehydrogenation (irrespective of whether it is conducted adiabatically or isothermally) can be performed either in a fixed catalyst bed or in a moving bed or fluidized bed. Performance in a fixed catalyst bed is normally preferred. All statements in this document therefore relate in particular to performance in a fixed catalyst bed.

Suitable catalyst charges for a conventional heterogeneously catalyzed dehydrogenation of a hydrocarbon to be dehydrogenated (e.g. propane) with a comparatively low conversion as described in single pass through the catalyst bed disposed in the particular reaction chamber are all catalysts disclosed as suitable in this document with regard to such a dehydrogenation, in particular those disclosed by way of example, and mixtures thereof with geometric shaped bodies which are inert with regard to the conventional heterogeneously catalyzed dehydrogenation.

A conventional heterogeneously catalyzed hydrocarbon (e.g. propane) dehydrogenation can be operated at catalyst loadings (based on the total amount of catalyst used), both with starting gas and with hydrocarbon to be dehydrogenated present therein (e.g. propane) of from 100 to 10 000 $h^{-1}$, frequently from 300 to 5000 $h^{-1}$, i.e. in many cases from 500 to 3000 $h^{-1}$, either at low (e.g. $\leq$30 mol %, or $\leq$20 mol %, or $\leq$15 mol %) or at high ($\geq$30 mol %) conversion of hydrocarbon to be dehydrogenated (e.g. propane).

A conventional heterogeneously catalyzed dehydrogenation of at least one hydrocarbon to be dehydrogenated (e.g. propane) can be implemented in a particular elegant manner (both at dehydrogenation conversions of $\leq$30 mol %, or $\leq$20 mol %, or $\leq$15 mol % and >30 mol % (e.g. 40 mol %, or 50 mol %)) in a staged reaction chamber.

Such a staged reaction chamber comprises more than one catalyst bed catalyzing the dehydrogenation in spatial succession. The number of catalyst beds may be, for example, from 1 to 20, appropriately from 2 to 8, but also from 3 to 6. The catalyst beds are preferably arranged in radial or axial succession. Appropriately from an application point of view, the fixed catalyst bed type is employed in such a staged reaction chamber.

In the simplest case, the fixed catalyst beds are arranged axially or in the annular gaps of concentric cylindrical grids in the reaction chamber. However, it is also possible to arrange the annular gaps in the reaction chamber in segments one on top of another, and to conduct the gas, after radial passage in one section, into the next segment up or down.

Appropriately, the reaction gas (starting gas), on its way from one catalyst bed to the next catalyst bed, is subjected to intermediate heating in the staged reaction chamber by passing it over heat exchanger ribs heated with hot gases or passing it through tubes heated with hot combustion gases or heat exchanger plates heated with hot gases.

When the process according to the invention in the staged reaction chamber is otherwise operated adiabatically, it is sufficient for dehydrogenation conversions (e.g. propane conversions) of $\leq$50 mol %, or $\leq$40 mol %, or $\leq$30 mol %, especially when using the catalysts described in DE-A 199 37 107, especially of the exemplary embodiments, to conduct the starting gas into the reaction chamber preheated to a temperature of from 400 or 450 to 550° C. (preferably from 400 to 500° C.) and to keep it at least within this temperature range within the staged reaction chamber. This means that the overall conventional dehydrogenation can thus be realized, at least with fresh catalysts, at comparatively moderate temperatures, which is found to be particularly favorable for the lifetime of the fixed catalyst beds between two regenerations.

It is even more beneficial to perform a conventional heterogeneously catalyzed dehydrogenation in the staged reactor described (as likewise already addressed) essentially autothermally, i.e. to perform the intermediate heating outlined above by a direct route (autothermal method).

To this end, molecular oxygen can advantageously be added to a limited extent to the reaction gas on its way through the fixed catalyst bed stages, for example after it passes through the first catalyst bed and between the subsequent catalyst beds. Depending on the dehydrogenation catalyst used, a limited combustion of the hydrocarbons present in the reaction gas, of any carbon or carbon-like compounds already deposited on the catalyst surface and/or of hydrogen which has been formed in the course of the conventional heterogeneously catalyzed dehydrogenation (e.g. of a propane dehydrogenation) and/or has been added to the reaction gas is thus brought about (it may also be appropriate, from an application point of view, to insert, in the staged reaction chamber, catalyst beds charged with catalyst which specifically (selectively) catalyzes the combustion of hydrogen (and/or of hydrocarbon) (useful such catalysts include, for example, those of documents U.S. Pat. No. 4,788,371, U.S. Pat. No. 4,886,928, U.S. Pat. No. 5,430,209, U.S. Pat. No. 5,530,171, U.S. Pat. No. 5,527,979 and U.S. Pat. No. 5,563,314; for example such catalyst beds may be accommodated in alternation to beds comprising the dehydrogenation catalyst in the staged reaction chamber)). The heat of reaction released thus enables (quasi-adiabatic reactor configuration), in a quasi-autothermal manner, a virtually isothermal (internal temperature control) operating mode of the heterogeneously catalyzed (e.g. propane) dehydrogenation. With increasing residence time selected for the reaction gas in the catalyst bed, (e.g. propane) dehydrogenation is thus possible with decreasing or essentially constant temperature, which enables particularly long lifetimes between two regenerations (instead of a staged reactor, it is also possible in an equivalent manner to employ a series connection of a number of reactors corresponding to the aforementioned number of stages, and to undertake the oxygen feeding between successive reactors in each case. The number of reactors thus connected may, for example be "three", or "two" or "four". In general, each individual reactor of these reactors has one fixed catalyst bed or at most two fixed catalyst beds).

A subsequent combustion, performed as described, of molecular hydrogen formed in the course of the dehydrogenation converts a nonoxidative conventional heterogeneously catalyzed dehydrogenation to an oxidative conventional heterogeneously catalyzed dehydrogenation in the context of the present application.

In general, oxygen feeding as described above should be undertaken such that the oxygen content of the reaction gas, based on the amount of hydrocarbon to be dehydrogenated and dehydrogenated hydrocarbon (e.g. propane and propylene) present therein, is from 0.01 or 0.5 to 30% by volume. The oxygen sources may be either pure molecular oxygen or oxygen diluted with inert gas, for example CO, $CO_2$, $N_2$, noble gases, but in particular also air. An alternative oxygen source may be nitrogen oxide. The resulting combustion gases generally have additional diluting action and thus promote the conventional heterogeneously catalyzed (e.g. propane) dehydrogenation.

The isothermicity of a conventional heterogeneously catalyzed (e.g. propane) dehydrogenation can be improved further by introducing closed internals (for example, tubular) which have favorably but not necessarily been evacuated before their filling in the reaction chamber comprising the catalyst bed stages in the spaces between the catalyst beds. Such internals may also be placed into the particular catalyst bed. These internals comprise suitable solids or liquids which evaporate or melt above a certain temperature and consume heat as they do so and, where the temperature goes below this temperature, condense again and release heat as they do so.

Another means of heating the starting gas or the starting gas stream for a conventional heterogeneously catalyzed (e.g. propane) dehydrogenation in the reaction chamber comprising the catalyst bed which catalyzes the dehydrogenation to the required reaction temperature consists in combusting a portion of the hydrocarbon to be dehydrogenated (e.g. of the propane) and/or $H_2$ present therein by means of molecular oxygen present in the starting gas on entry into the reaction chamber (for example over suitable specific combustion catalysts, for example by simply passing it through and/or passing it over) and, by means of the heat of combustion thus released, bringing about the heating to the reaction temperature desired (for the dehydrogenation). The resulting combustion products, such as $CO_2$, $H_2O$ and the $N_2$ which may accompany the molecular oxygen required for the combustion, are advantageous inert diluent gases.

The aforementioned hydrogen combustion can be implemented in a particularly elegant manner as described in WO 03/076370 or DE-A 102 11 275. In other words, in a process for continuous conventional oxidative heterogeneously catalyzed partial dehydrogenation of hydrocarbon to be dehydrogenated (e.g. in propane) over at least one catalyst bed disposed in a reaction chamber, in which at least one starting gas stream comprising at least one hydrocarbon to be dehydrogenated (e.g. propane), molecular oxygen, molecular hydrogen and, if appropriate, steam is fed continuously to the reaction chamber, in the reaction chamber, the at least one hydrocarbon to be dehydrogenated is conducted through at least one catalyst bed disposed in the reaction chamber, over which molecular hydrogen and, at least partially, at least one dehydrogenated hydrocarbon (e.g. propylene) are formed by conventional heterogeneously catalyzed dehydrogenation, further gas comprising molecular oxygen is added if appropriate to the reaction gas on its way through the reaction chamber after it has entered the inventive reaction chamber, the molecular oxygen in the molecular hydrogen present in the reaction gas in the reaction chamber is oxidized at least partly to steam, and at least one product gas stream which comprises molecular hydrogen, steam, dehydrogenated hydrocarbon (e.g. propylene) and hydrocarbon to be dehydrogenated (e.g. propane) is withdrawn continuously from the reaction chamber, wherein the at least one product gas stream withdrawn from the reaction chamber is divided into two portions of identical composition and one of the two portions is recycled as dehydrogenation cycle gas into the at least one starting gas stream fed to the inventive reaction chamber, and the other portion is used further in another way (for example, for the purpose of a heterogeneously catalyzed partial oxidation of dehydrogenated hydrocarbon formed in the reaction chamber).

At this point, it should be emphasized that the starting gas stream (the reaction gas mixture stream fed to the catalyst bed which catalyzes the dehydrogenation) of an oxidative or nonoxidative conventional heterogeneously catalyzed partial dehydrogenation of a hydrocarbon to be dehydrogenated comprises generally $\geq 5\%$ by volume of the hydrocarbon to be dehydrogenated (e.g. propane). Frequently, this proportion by volume is at values on a corresponding basis of $\geq 10\%$ by volume, often $\geq 15\%$ by volume and usually $\geq 20\%$ by volume, or $\geq 25\%$ by volume or $\geq 30\%$ by volume. Frequently, this proportion by volume is, however, at values on the same basis of $\leq 90\%$ by volume, usually $\leq 80\%$ by volume and often $\leq 70\%$ by volume. The above data apply especially in the case of propane as the hydrocarbon to be dehydrogenated and propylene as the dehydrogenated hydrocarbon. Of course, they also apply when isobutane is the hydrocarbon to be dehydrogenated and isobutene is the dehydrogenated hydrocarbon. In addition, it (the starting gas stream) may, for example comprise:
a) $N_2$ and $H_2O$;
b) $N_2$, $O_2$ and $H_2O$;
c) $N_2$, $O_2$, $H_2O$ and $H_2$;
d) $N_2$, $O_2$, $H_2O$, $H_2$ and $CO_2$;
e) $N_2$, $O_2$, $H_2O$, $H_2$, $CO_2$ and CO.

In the case of an oxidative conventional heterogeneously catalyzed partial dehydrogenation of a hydrocarbon to be dehydrogenated, the oxygen source used may be pure molecular oxygen, air or other mixtures of molecular oxygen and inert gas.

The increasing deactivation of the catalyst bed which accompanies increasing operating time of a conventional partial heterogeneously catalyzed dehydrogenation of a hydrocarbon to be dehydrogenated can be counteracted especially as described in DE-A 10 2006 035 718 (for example increasing the reaction temperature by internal and/or external temperature control).

However, the measures to be taken in this regard are generally also accompanied by an increase in undesired by-product formation, which is why the regenerating use of the inventive procedure after a certain operating time is advantageous.

When the heterogeneously catalyzed partial dehydrogenation has been performed in a staged reactor which comprises, in flow direction of the reaction gas, a sequence of a plurality of spatially successive catalyst beds (catalyst bed stages), the inventive regeneration of the overall (fixed) catalyst bed can in principle be effected in different ways.

Firstly, the regeneration of the overall catalyst bed (i.e. the entirety of all individual catalyst beds present in the staged reactor) can be undertaken as such. In other words, the regeneration gas is fed to the staged reactor with the appropriate temperature, and conducted successively through each individual catalyst bed within the staged reactor according to the spatial succession of the individual catalyst beds. The overall catalyst bed is then regenerated entirely analogously to the regeneration of an individual deactivated catalyst bed (the sum of the individual beds effectively forms the catalyst bed to be regenerated).

In principle, in a staged reactor, the possibility also exists of regenerating each individual catalyst bed, each individual catalyst bed stage, alone in the inventive manner. Appropriately, from an application point of view, the procedure in this case will be to begin with the regeneration of the last catalyst bed in flow direction (the last catalyst bed stage in flow direction). In other words, the regeneration gas is fed in between the last and second-to-last catalyst bed in the flow direction, and passed exclusively through the last catalyst bed. On completion of regeneration of the last catalyst bed in flow direction, the regeneration is continued with the regeneration of the second-to-last catalyst bed in flow direction, etc. In other words, the regeneration gas is then fed between the third-to-last catalyst bed in flow direction and the second-to-last catalyst bed in flow direction, and conducted first through the second-to-last catalyst bed in flow direction and, flowing out of this, through the last catalyst bed in flow direction, etc. In an entirely corresponding manner, it is also possible for the catalyst beds which catalyze the dehydrogenation and are distributed between a series connection of different dehydrogenation reactors to be regenerated in accordance with the invention. However, it will be appreciated that catalyst beds present in different dehydrogenation reactors (irrespective of their connection) may also be regenerated in accordance with the invention independently of one another and simultaneously.

For the performance of a conventional (oxidative or non-oxidative) heterogeneously catalyzed dehydrogenation, especially for an adiabatic operating mode, the interior of a single shaft furnace ("shaft furnace reactor") is sufficient as the reaction chamber comprising at least one catalyst bed (for example the at least one fixed catalyst bed), which is flowed through axially and/or radially by the starting gas stream. A particularly preferred embodiment of such a reactor is described by DE-A 10 2006 029 790, DE-A 10 2006 035 718, DE-A 10 2006 017 623.5 and DE-A 10 2006 015 235.2.

In the simplest case, the vessel is, for example, an essentially cylindrical vessel whose internal diameter is from 0.1 to 10 m, possibly from 0.5 to 5 m, and in which the at least one fixed catalyst bed is mounted on a support device (for example, a grid). The reaction chamber charged with catalyst whose inventive shell in adiabatic operation is additionally thermally insulated against its environment by application of appropriate insulation materials (for example glass wool), is appropriately flowed through axially with the hot starting gas stream comprising the hydrocarbon to be dehydrogenated (e.g. the propane). The catalyst geometry may be either spherical or annular, or strand-shaped. Since the reaction chamber in the case just described can be realized by very inexpensive apparatus, all catalyst geometries which have a particularly low pressure drop are preferable. These are in particular catalyst geometries which lead to a high cavity volume or are structured, for example monoliths or honeycombs. For the realization of a radial flow of the reaction gas comprising the hydrocarbon to be dehydrogenated (e.g. the propane), the inventive reaction chamber may, for example, comprise two concentric cylindrical grids and the catalyst bed may be arranged in their annular gap. In the adiabatic case, the shell surrounding it (the jacket shell) would, if appropriate, in turn be thermally insulated. In the case of an essentially cylindrical shaft furnace flowed through axially, it is advantageous for the process according to the invention in the case of an adiabatic operating mode when the dimension A of the reaction chamber at right angles to the cylindrical axis is at least 5 times, preferably at least 10 times and more preferably at least 15 times the bed height S of the at least one catalyst bed in axial direction. In general, the aforementioned ratio of A:S will, however, be $\leq 200$, typically $\leq 150$ and usually $\leq 100$.

A heterogeneously catalyzed oxydehydrogenation which causes the deactivation of the catalyst bed to be regenerated in accordance with the invention and precedes the inventive regeneration can in principle be performed as described, for example in the documents U.S. Pat. No. 4,788,371, CN-A 1073893, Catalysis Letters 23 (1994), 103-106, W. Zhang, Gaodeng Xuexiao Huaxue Xuebao, 14 (1993) 566, Z. Huang, Shiyou Huagong, 21 (1992) 592, WO 97/36849, DE-A 197 53 817, U.S. Pat. No. 3,862,256, U.S. Pat. No. 3,887,631, DE-A 195 30 454, U.S. Pat. No. 4,341,664, J. of Catalysis 167, 560-569 (1997), J. of Catalysis 167, 550-559 (1997), Topics in Catalysis 3 (1996) 265-275, U.S. Pat. No. 5,086, 032, Catalysis Letters 10 (1991), 181-192, Ind. Eng. Chem. Res. 1996, 35, 14-18, U.S. Pat. No. 4,255,284, Applied Catalysis A: General, 100 (1993), 111-130, J. of Catalysis 148, 56-67 (1994), V. Cortés Corberán and S. Vic Bellón (Ed.), New Developments in Selective Oxidation II, 1994, Elsevier Science B.V., S. 305-313, $3^{rd}$ World Congress on Oxidation Catalysis, R. K. Grasselli, S. T. Oyama, A. M. Gaffney and J. E. Lyons (Ed.), 1997, Elsevier Science B.V., S. 375ff or in DE-A 198 37 520, DE-A 198 37 517, DE-A 198 37 519 and DE-A 198 37 518, using the example of the heterogeneously catalyzed partial oxydehydrogenation of propane.In this case, the oxygen source used may, for example, be air. The oxygen source used here as well as inert gas, however, frequently has molecular oxygen to an extent of at least 90 mol %, and in many cases molecular oxygen to an extent of at least 95 mol %. In principle, the oxygen source used may also be pure molecular oxygen.

The catalysts suitable for the heterogeneously catalyzed oxydehydrogenation are not subject, as already stated, to any particular restrictions. Suitable oxydehydrogenation catalysts are all of those known to the person skilled in the art in this field which are capable of oxidizing, for example, propane to propylene. In particular, all oxydehydrogenation catalysts mentioned in the aforementioned documents may be used. Suitable catalysts are, for example, oxydehydrogenation catalysts which comprise at least V and Mg, or at least V and Sb, or at least V, Sb and Mg, but also oxydehydrogenation catalysts which comprise MoVNb oxides or vanadyl pyrophosphate, in each case if appropriate with promoter. One example of a favorable oxydehydrogenation catalyst is a catalyst which comprises a mixed metal oxide I with Mo, V, Te, O and X as essential constituents, where X is at least one element selected from niobium, tantalum, tungsten, titanium, aluminum, zirconium, chromium, manganese, gallium, iron, ruthenium, cobalt, rhodium, nickel, palladium, platinum, antimony, bismuth, boron, indium, silicon, lanthanum, sodium, lithium, potassium, magnesium, silver, gold and cerium (see also EP-A 938463 and EP-A 167109). Further particularly suitable oxydehydrogenation catalysts are the multimetal oxide compositions or catalysts A (referred to in this document as multimetal oxide compositions II) of DE-A-197 53 817 and the catalysts of DE-A 19838312, the multimetal oxide compositions or catalysts A mentioned as preferred in the first document being very particularly favorable. Thus, useful active compositions for a heterogeneously catalyzed oxydehydrogenation of a hydrocarbon to be dehydrogenated include multimetal oxide compositions of the general formula III $$M^1{}_a Mo_{1-b} M^2{}_b O_x \qquad (III)$$

where
$M^1$=Co, Ni, Mg, Zn, Mn and/or Cu,
$M^2$=W, V, Te, Nb, P, Cr, Fe, Sb, Ce, Sn and/or La,
a=0.5-1.5,
b=0-0.5,
and
x=a number which is determined by the valency and frequency of the elements in (III) other than oxygen.

They can be prepared and shaped as described in DE-A 102 45 585.

For a heterogeneously catalyzed oxydehydrogenation of, for example, propane, the reaction temperature when using fresh catalysts is preferably in the range from 200 to 600° C., especially in the range from 250 to 500° C., more preferably in the range from 350 to 440° C. The working pressure is preferably in the range from 0.5 to 10 bar, in particular from 1 to 10 bar, more preferably from 1 to 5 bar. Working pressures above 1 bar, for example from 1.5 to 10 bar, have been found to be particularly advantageous. In general, the heterogeneously catalyzed oxydehydrogenation of, for example, propane (propane is always mentioned here as a representative of all other hydrocarbons to be dehydrogenated) is also effected over a fixed catalyst bed. The latter is appropriately poured into the tubes (together with the two tube orifices, the tube wall forms the shell in contact with the reaction chamber; the tube interior is the reaction chamber) of a, for example, salt bath-cooled tube bundle reactor (generally disposed on a gas-permeable grid), as described, for example, in EP-A 700 893 and in EP-A 700 714 and the literature cited in these documents. The starting gas stream is fed to the tube inlet. The mean residence time of the reaction gas in the catalyst bed is appropriately from 0.5 to 20 seconds. The ratio of, for example, propane to oxygen varies with the desired conversion and the selectivity of the catalyst. Appropriately, it is within the range from 0.5:1 to 40:1, in particular from 1:1 to 15:1, more preferably from 2:1 to 6:1 or to 5:1. In general, the propylene selectivity decreases with rising propane conversion. Preference is therefore given to performing the propane to propylene reaction in such a way that relatively low conversions with propane are achieved at high selectivities for propylene. More preferably, the conversion of propane is in the range from 5 to 40 mol %, frequently in the range from 10 to 30 mol %. In this context, the term "propane conversion" means the proportion of propane fed in which is converted in single pass of the reaction gas through the tube. In general, the selectivity of propylene formation is from 50 to 98 or to 99 mol %, more preferably from 80 to 98 or 99 mol %, the term "selectivity" referring to the moles of propylene obtained per mole of propane converted, expressed as a molar percentage. In the reaction tube, the reaction temperature generally passes through a maximum.

In general, the starting gas stream used in a heterogeneously catalyzed propane oxydehydrogenation comprises from 5 to 95 mol % of propane (based on 100 mol % of starting gas). In addition to propane (or another hydrocarbon to be oxydehydrogenated) and oxygen, the starting gas for the heterogeneously catalyzed oxydehydrogenation may also comprise further, especially inert, constituents such as carbon dioxide, carbon monoxide, nitrogen, noble gases, other hydrocarbons, for example secondary constituents present in the crude propane (the propane source used for the process according to the invention is normally crude propane, as recommended, for example, in DE-A 102 45 585 and in DE-A 10 2005 022 798), and/or propylene. The heterogeneously catalyzed oxydehydrogenation can also be performed in the presence of diluents, for example steam.

Any desired reactor sequence which is known to those skilled in the art can be used to perform the heterogeneously catalyzed oxydehydrogenation of, for example, propane. For example, the heterogeneously catalyzed oxydehydrogenation can be performed in a single reactor or in a battery of two or more reactors between which oxygen is supplied if appropriate.

As possible constituents, the product gas of a heterogeneously catalyzed propane oxydehydrogenation to be performed as described may, for example, comprise the following constituents: propylene (as the target product, i.e. as the dehydrogenated hydrocarbon), propane (as the unconverted hydrocarbon to be dehydrogenated), carbon dioxide, carbon monoxide, water, nitrogen, oxygen, ethane, ethene, methane, acrolein, acrylic acid, methacrolein, methacrylic acid, furfurals, ethylene oxide, butane (e.g. n-butane or isobutane), acetic acid, formaldehyde, formic acid, propylene oxide and butenes (e.g. butene-1). In this context, ethane, ethene and methane in particular are possible thermal decomposition products of propane. Typically, a product gas obtained in an inventive heterogeneously catalyzed propane oxydehydrogenation comprises: from 5 to 10 mol % of propylene, from 0.1 to 2 mol % of carbon monoxide, from 1 to 3 mol % of carbon dioxide, from 4 to 10 mol % of water, from 0 to 10 or to 1 mol % of nitrogen, from 0.01 (or 0) to 0.5 mol % of acrolein, from 0.01 (or 0) to 1 mol % of acrylic acid, from 0.05 (or 0) to 2 mol % of acetic acid, from 0.01 to 0.05 mol % of formaldehyde, from 1 to 5 mol % of oxygen, from 0.1 to 10 mol % of further abovementioned constituents, and also as the remainder, essentially propane, based in each case on 100% product gas.

Heterogeneously catalyzed oxydehydrogenations of hydrocarbons to be dehydrogenated other than propane can be performed in accordance with the invention in a manner corresponding to that described above for the oxydehydrogenation of propane. Possible such hydrocarbons to be oxydehydrogenated include in particular butane (to butene (in particular isobutane to isobutene) and/or butadiene) and butenes (to butadiene).

Frequently, the oxidative or nonoxidative heterogeneously catalyzed dehydrogenation of the hydrocarbon to be dehydrogenated will be followed by a process for heterogeneously catalyzed partial oxidation of dehydrogenated hydrocarbon generated therein (e.g. propylene to acrolein and/or acrylic acid), preferably accompanied by hydrocarbon to be dehydrogenated which has not been converted in the dehydrogenation (e.g. propane) as an inert gas with regard to such a partial oxidation.

In this case, the product gas stream A withdrawn (continuously) from the dehydrogenation will be used, as such or after removal of at least a portion of its constituents (e.g. $H_2$, $H_2O$, $N_2$, etc.) other than the dehydrogenated hydrocarbon (e.g. propylene) and other than the (unconverted) hydrocarbon to be dehydrogenated (e.g. propane), to charge at least one oxidation reactor, and the dehydrogenated hydrocarbon (e.g. propylene) present in the charge gas mixture will be subjected to a selective heterogeneously catalyzed partial gas phase oxidation with molecular oxygen to give a product gas mixture B comprising the (partial oxidation product) target product (e.g. acrolein, or acrylic acid or a mixture thereof), and also generally unconverted hydrocarbon to be dehydrogenated (e.g. propane) and excess molecular oxygen, with or without unconverted dehydrogenated hydrocarbon (e.g. propylene).

In a downstream separating zone B, targets product present in product gas mixture B (e.g. acrolein or acrylic acid, or a mixture thereof) will be removed and at least a portion comprising unconverted hydrocarbon to be dehydrogenated (e.g. propane), and, if appropriate, unconverted molecular oxygen and, if appropriate, unconverted dehydrogenated hydrocarbon (e.g. propylene) from the remaining residual gas which comprises unconverted hydrocarbon to be dehydrogenated (e.g. propane) and molecular oxygen, with or without unconverted dehydrogenated hydrocarbon (e.g. propylene) will be recycled as partial oxidation cycle gas into the dehydrogenation (for example as a constituent of the starting gas stream).

When the dehydrogenation is, for example, an oxidative conventional heterogeneously catalyzed partial dehydrogenation of propane to propylene, and the subsequent partial oxidation is that of propylene to acrolein or to acrylic acid or to a mixture thereof, the starting gas stream fed to the oxidative dehydrogenation may comprise, for example, as essential contents:

| | |
|---|---|
| Propylene | $\geq 0$ to 20 or to 10, frequently 0 to 6% by volume, |
| Acrolein | $\geq 0$ to 1, in many cases 0 to 0.5, frequently 0 to 0.25% by volume, |
| Acrylic acid | $\geq 0$ to 0.25 (or to 0.4), in many cases 0 to 0.05, frequently 0 to 0.03% by volume, |
| $CO_x$ | $\geq 0$ to 20 or to 5, in many cases 0 to 3, frequently 0 to 2% by volume, |
| Propane | 5 to 50, preferably 20 to 40% by volume, |
| Nitrogen | 20 or 30 to 80, preferably 50 to 70% by volume, |
| Oxygen | $\geq 0$ to 5, preferably 1.0 to 2.0% by volume, |

-continued

| | |
|---|---|
| $H_2O$ | $\geq 0$ to 20, preferably 5.0 to 10.0% by volume, and |
| $H_2$ | $\geq 0$, frequently $\geq 0.01$, often $\geq 0.05$ to 10, preferably 1 to 5% by volume. |

Acetic acid may also be present in small amounts (approximately comparable to the possible acrylic acid contents).

The constituents in the starting gas stream fed to the dehydrogenation which originate from the partial oxidation of the dehydrogenated hydrocarbon are capable in turn of contributing to the deactivation of the catalyst (catalyst bed) used in the dehydrogenation. The regeneration process according to the invention is, however, found to be effective in these cases too.

For example, descriptions of such multistage processes can be found in the documents DE-A 10 2006 029 790, DE-A 10 2006 035 718, DE-A 10 2005 022 798, DE 10 2006 024 901.1, DE-A 102 46 119, DE-A 102 45 585, DE-A 10 2005 049 699, DE-A 10 2004 032 129, DE-A 10 2005 013 039, DE-A 10 2005 010 111, DE-A 10 2005 009 891, DE-A 102 11 275, EP-A 117 146, U.S. Pat. No. 3,161,670, DE-A 33 13 573, WO 01/96270, DE-A 103 16 039, DE-A 102 19 686, DE-A 10 2005 009 885, DE-A 10 2005 052 923, DE-A 10 2005 057 197, WO 03/076370, DE-A 102 45 585, DE-A 22 13 573, U.S. Pat. No. 3,161,670 and the prior art cited in these documents.

The advantageousness of the regeneration process according to the invention is thought to be based on the fact that the different carbon-rich species which are contributory causes of deactivation and are deposited on and in the (fixed) catalyst bed in the course of the deactivation can effectively be burnt off gradually (successively, in succession). The process according to the invention is also notable in particular in that the deactivation behavior of the catalyst bed regenerated in accordance with the invention essentially does not differ from the deactivation behavior of the freshly charged catalyst bed. Operating times of from 30 to 100 h between two regenerations are typical.

WORKING EXAMPLE AND COMPARATIVE EXAMPLES

I. Working Example a) Description of the Dehydrogenation Reactor

The dehydrogenation reactor used was a steel tube (stainless steel of DIN materials number 1.4841) of length 2070 mm, of wall thickness 1 mm and of internal diameter 36.4 mm. The tubular reactor was flowed through by the reaction gas mixture stream from the top downward. A 115 mm-high catalyst base made of the same stainless steel projected into the lower end of the tubular reactor, and supported the overall fixed catalyst bed (consisting of three partial fixed catalyst beds of approximately identical bulk density) in a structured manner from the top downward as follows:

| | |
|---|---|
| 790 mm | bed length of (inert) steatite spheres (diameter 4-5 mm) of C-220 steatite from CeramTec (internal heating bed); |
| 195 mm | bed length of dehydrogenation catalyst (Pt/Sn alloy which had been promoted with the elements Cs, K and La in oxidic form and which had been applied to the outer and inner surface of $ZrO_2 \cdot SiO_2$ mixed oxide support extrudates (mean length (Gaussian distribution in the range from 3 mm to 12 mm with maximum at approx. 6 mm): 6 mm, diameter: 2 mm) in |

-continued

| | |
|---|---|
| | the elemental stoichiometry (mass ratio including support) $Pt_{0.3}Sn_{0.6}La_{3.0}Cs_{0.5}K_{0.2}(ZrO_2)_{88.3}(SiO_2)_{7.1}$ (catalyst precursor preparation and activation to the active catalyst as in example 4 of DE-A 102 19 879); |
| 145 mm | bed length of steatite spheres (diameter 4-5 mm) of C-220 steatite from CeramTec; |
| 190 mm | bed length of the aforementioned dehydrogenation catalyst; |
| 145 mm | bed length of steatite spheres (diameter 4-5 mm) of C-220 steatite from CeramTec; |
| 195 mm | bed length of the aforementioned dehydrogenation catalyst; |
| 20 mm | bed length of steatite spheres (diameter 1.5-2.5 mm) of C-220 steatite from CeramTec; and |
| 210 mm | bed length of steatite spheres (diameter 4-5 mm) of C-220 steatite from CeramTec. |

Above the internal heating bed, the steel tube was empty.

The tubular reactor was inserted externally, for the purpose of a preheating zone, for the length of the uppermost 400 mm of the heating bed from the top downward (toward the catalyst base), into two half-shells made of copper (thickness of shell=25 mm) which ensure equal distribution of the amount of heat supplied, which were electrically heated by means of a heating band completely surrounding them. A winding of thermoelectric insulation material was present around the heating band.

From the bottom upward (beginning just below the catalyst base surface), the tubular reactor was inserted for a length of 1530 mm into two pairs of thermally insulating half-shells (thickness of one half-shell=25 mm) made of MPS-Super G from Microtherm in Germany, which were mounted offset by 90° relative to one another. The insulating half-shells were in turn surrounded by a cylindrical shell of stainless steel (external diameter=168 mm, internal diameter=154 mm), around which a radiative oven (length=1600 mm) was arranged for the purpose of trace heating. In this way, the heat flux from the environment into the reaction tube and out of the reaction tube into the environment was minimized along the adiabatic zone.

In addition, a 2500 mm-long thermowell (external diameter=6 mm; internal diameter=4 mm) was introduced into the middle (center) of the reaction tube, into which a multiple thermoelement (a total of 14 measurement points every 8 cm from the lower reactor end upward, thickness 3.2 mm) was introduced.

In addition, two lance pairs had been introduced into the tubular reactor. One pair had been introduced into the tubular reactor from the bottom and the other pair from the top. The lances of one pair were each conducted adjacently between thermowell and internal reactor wall in such a way that they were positioned in the middle between thermowell and internal reactor wall over the tube cross section. Projected into a tubular cross-sectional plane, the two pairs were opposite one another on a tube diameter. The external diameter of a lance manufactured from stainless steel of DIN materials number 1.4841 was 3.17 mm and its internal diameter was 2.17 mm. The length of the lances of one pair was different. Air was metered in through one of the two lances of a lance pair in each case, and reaction gas mixture was withdrawn for analysis purposes through the other lance in each case of a lance pair. The opening of the first analysis lance (LI) in flow direction was placed 20 mm beyond the first partial fixed catalyst bed in flow direction. The opening of the accompanying metering lance (ZI) was placed 100 mm upstream of the second partial fixed catalyst bed in flow direction. The opening of the second analysis lance (LII) in flow direction was placed 20 mm beyond the second partial fixed catalyst bed in flow direction. The opening of the accompanying metering lance (ZII) was placed 100 mm upstream of the third partial fixed catalyst bed in flow direction.

Upstream of the tubular reactor, a steel tube of length 1300 mm filled with steatite spheres (of C-220 steatite from CeramTec, diameter 4-5 mm) was inserted as a heater. The reaction gas mixture stream was preheated therein to its entrance temperature into the tubular reactor and simultaneously mixed ideally. For this purpose, the heater tube (stainless steel of DIN materials number 1.4841, wall thickness 3.6 mm, internal diameter 53.1 mm) was heated electrically at a midpoint length of 1200 mm by means of heating collars applied around it from Horst, Heidelberg, Germany. The connection between heater and tubular reactor was accomplished by means of a thermally heated stainless steel tube thermally insulated with customary thermal insulation materials (stainless steel of DIN materials number 1.4841, external diameter 14 mm, internal diameter 10 mm, length 300 mm).

b) Beginning of the Long-Term Operation (Operating Time $t_0$) of the Heterogeneously Catalyzed Partial Dehydrogenation of Propane The overall catalyst bed was charged with fresh dehydrogenation catalyst. The reaction gas mixture stream supplied to the overall fixed catalyst bed was a mixture of crude propane, steam and partial oxidation cycle gas of a heterogeneously catalyzed two-stage partial oxidation of the propylene obtained in the dehydrogenation to acrylic acid. The constituents other than propane and propylene were removed from the product gas mixture of the dehydrogenation as described in comparative example 1 of German application 10 2005 013 039 by absorptive/desorptive means (stripping with air). The partial oxidation of propylene to acrylic acid was likewise effected as described in German application 10 2005 013 039. The same applies to the formation of the partial oxidation cycle gas.

As described in German application 10 2005 013 039, the reaction gas mixture stream was obtained in an evaporator with an exit temperature of about 200° C. and supplied starting from there to the heater (the attachment of the evaporator to the heater was configured like that of the heater to the tubular reactor).

The heating of the heater was controlled in such a way that the reaction gas mixture stream passed from the evaporator into the heater left it with a temperature of about 400° C. The reaction gas mixture stream was then conducted into the tubular reactor and heated further in the preheating zone thereof and finally conducted through the tubular reactor. In each case about 30 l (STP)/h of air which had a temperature of 25° C. on entry into the particular lance were metered in via the metering lances ZI and ZII. After an operating time of to =1 h, the process operation attained its (quasi-)steady operating state essentially for the first time.

The contents of the reaction gas mixture stream supplied to the tubular reactor (all gas composition data in this document are always based on gas chromatography analysis) of 2807 l (STP)/h and the contents of the reaction gas mixture stream when leaving the first, second and third partial fixed catalyst bed in flow direction were as reported in table 1.

TABLE 1

|  | Reactor inlet | After 1st partial bed | After 2nd partial bed | After 3rd partial bed |
|---|---|---|---|---|
| ppm by vol. of acrolein | 235 | <2 | <2 | <2 |
| ppm by vol. of acrylic acid | 344 | <2 | <2 | <2 |
| ppm by vol. of acetic acid | 170 | <2 | <2 | <2 |
| % by vol. of hydrogen | 0.05 | 2.42 | 3.15 | 4.37 |
| % by vol. of oxygen | 2.93 | <2 | <2 | <2 |
| % by vol. of nitrogen | 53 | 51 | 51 | 51 |
| % by vol. of carbon monoxide | 0.36 | 0.15 | 0.16 | 0.18 |
| % by vol. of carbon dioxide | 1.29 | 2.20 | 2.53 | 2.48 |
| ppm by vol. of methane | 39 | 175 | 342 | 386 |
| ppm by vol. of ethane | 305 | 313 | 357 | 447 |
| ppm by vol. of ethene | 328 | 397 | 565 | 599 |
| ppm by vol. of acetylene | 2 | 14 | 25 | 26 |
| % by vol. of propane | 35.4 | 32.5 | 29.6 | 27.8 |
| ppm by vol. of cyclopropane | 200 | 85 | 35 | 19 |
| % by vol. of propene | 0.34 | 4.92 | 6.90 | 7.33 |
| ppm by vol. of propadiene | <2 | <2 | <2 | <2 |
| ppm by vol. of propyne | <2 | 28 | 50 | 52 |
| ppm by vol. of isobutane | 71 | 63 | 57 | 51 |
| ppm by vol. of n-butane | 3 | 3 | 3 | 3 |
| ppm by vol. of trans-butene-2 | 2 | 2 | 2 | 3 |
| ppm by vol. of butene-1 | <2 | <2 | 2 | 3 |
| ppm by vol. of isobutene | 5 | 7 | 12 | 17 |
| ppm by vol. of cis-butene-2 | <2 | <2 | 2 | 2 |
| ppm by vol. of butadiene-1,3 | 7 | 2 | 2 | 2 |
| ppm by vol. of other $C_2$-$C_4$ hydrocarbons | <2 | <2 | <2 | <2 |
| ppm by vol. of benzene | 83 | 69 | 69 | 78 |
| ppm by vol. of total remaining $C_5$ hydrocarbons | 34 | 9 | 10 | 17 |
| ppm by vol. of total remaining $C_6$ hydrocarbons | 8 | 7 | 7 | 5 |

Remaining amount up to 100% by volume = in each case water

As the reaction gas mixture stream passes through the overall catalyst bed, a total of G=(A+B+C) mol % of the molar starting amount HC of hydrocarbon to be dehydrogenated present therein was dehydrogenated to dehydrogenated hydrocarbon. A is the contribution of the first partial fixed catalyst bed in flow direction, B is the contribution of the second partial fixed catalyst bed in flow direction and C is the contribution of the third partial fixed catalyst bed in flow direction.

At the operating time to, the numerical values of G, A, B and C were as follows:

A=12 mol %,
B=5.4 mol %,
C=1.8 mol %, and
G=19.2 mol %,
based in each case on HC.

The temperature $T_1$ of the reaction gas mixture stream in flow direction immediately beyond the internal heating bed in the tubular reactor at the operating time to was 408° C. The air streams MI and MII metered in via ZI and ZII at the operating time to were in each case approx. 33 l (STP)/h.

c) Performance of the Long-Term Operation of the Heterogeneously Catalyzed Partial Dehydrogenation of Propane

DESCRIPTION OF THE DRAWINGS

Figure 2:
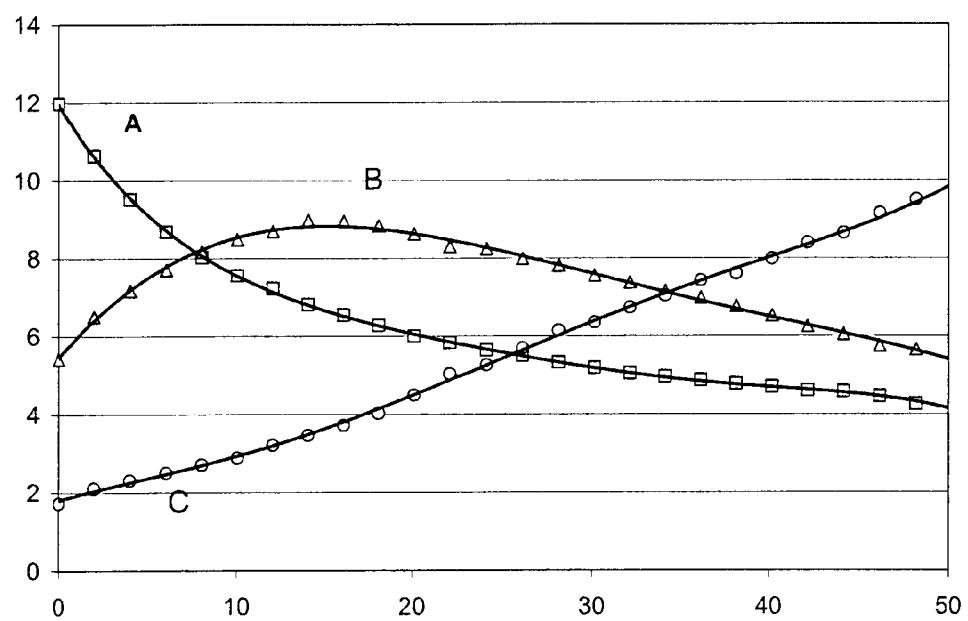
FIG. 2: raised conversion (mole % of HC) in operating time intervals.

In order to counteract deactivation of the overall fixed catalyst bed which accompanies increasing operating time, both $T_1$ and MI (=M1 in FIG. 1) and MII (=M2 in FIG. 1) were raised gradually with increasing operating time as shown in FIG. 1 (by the raised data points) (left-hand ordinate=$T_1$ in ° C.; right-hand ordinate=air flow rate in l (STP)/h; the zero point was placed at to; the abscissa shows t in h). In this manner, it was possible to keep the value for G stable within the interval G=19.2±0.2 mol % over the operating time interval 0 h=$t_0$<t≦50 h. The resulting profile against time (the abscissa shows t in h) of the raised conversion proportions A, B, C (mol % of HC as the ordinate) in the operating time interval is shown by FIG. 2.

Figure 3:
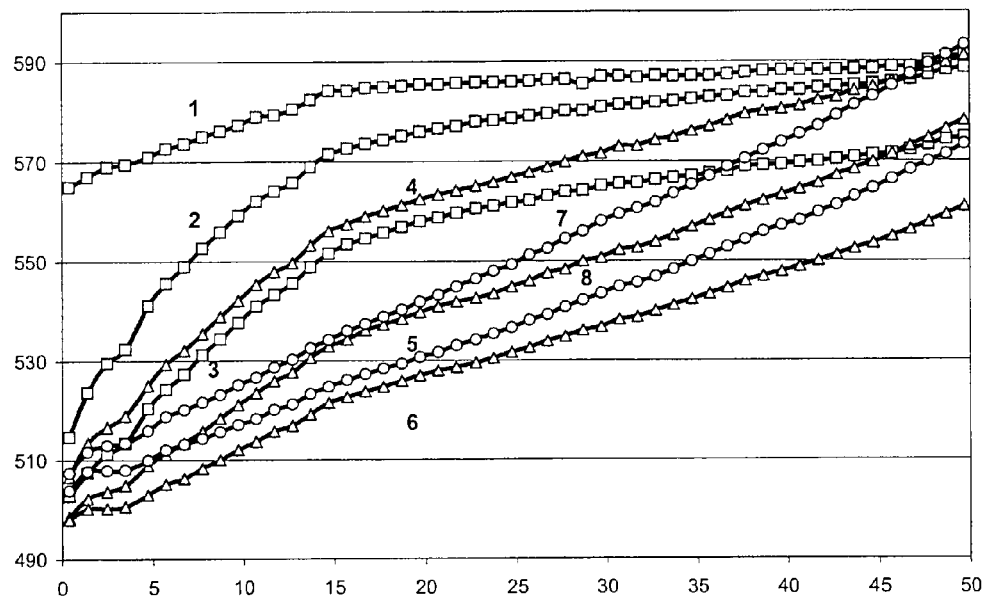
FIG. 3: partial catalyst bed in flow direction against time.

The resulting profile of the temperature of the reaction gas mixture stream just beyond the inlet (the maximum temperature in the partial bed, reference numeral 1), in the middle (reference numeral 2) and at the outlet (reference numeral 3) of the first partial fixed catalyst bed in flow direction against time is shown (by the raised measurements) in FIG. 3 (the abscissa again shows t in h, the zero point was placed at to, and the ordinate shows T in ° C.), as is the profile of the temperature of the reaction gas mixture stream just beyond the inlet (the maximum temperature in the partial bed, reference numeral 4), in the middle (reference numeral 5) and at the outlet (reference numeral 6) of the second partial fixed catalyst bed in flow direction and of the third partial fixed catalyst bed in flow direction against time (reference numeral 7=the maximum temperature in the third partial fixed catalyst bed just beyond the inlet into it, reference numeral 8=just beyond the outlet of the third partial fixed catalyst bed).

d) Performance of an Inventive Regeneration

After an operating time of t=$t_0$+50 h, the air streams MI and MII were interrupted and the reaction gas mixture stream fed to the tubular reactor was replaced by a nitrogen stream to flush the catalyst bed. The purity of the nitrogen stream was ≧99.9% by volume.

The nitrogen flow rate was 3930 l (STP)/h. The heating by means of heater and preheating zone was controlled such that the temperature of the nitrogen stream in flow direction immediately beyond the internal heating bed in the tubular reactor was 450° C. The exit pressure of the nitrogen stream at the outlet of the tubular reactor was 2 bar above atmospheric pressure. The exit pressure was controlled by means of a pressure-retaining control valve.

The aforementioned conditions were retained over a period of 10 h. Subsequently, the nitrogen stream was replaced by 4102 l (STP)/h of a mixture of 3930 l (STP)/h of nitrogen stream and 172 l (STP)/h of air. The temperature of this regeneration gas stream was likewise adjusted to 450° C. in flow direction immediately beyond the internal heating bed. The exit pressure of the regeneration gas stream at the outlet of the tubular reactor was 3.5 bar above atmospheric pressure.

The aforementioned conditions were retained over a period of 24 min. Then, while retaining the other regeneration conditions, the composition and the magnitude of the regeneration gas stream were changed in the sequence listed below in each case for a period t:

| Time t (min) | Regeneration gas stream (l (STP)/h) | Air stream content (l (STP)/h) | Nitrogen stream content (l (STP)/h) |
|---|---|---|---|
| 5 | 4145 | 215 | 3930 |
| 9 | 4253 | 323 | 3930 |
| 7 | 4360 | 430 | 3930 |
| 2 | 4468 | 538 | 3930 |
| 4 | 4576 | 646 | 3930 |
| 4 | 4791 | 861 | 3930 |
| 5 | 5006 | 1076 | 3930 |
| 6 | 5545 | 1615 | 3930 |
| 4 | 4845 | 1615 | 3230 |
| 3 | 4307 | 1615 | 2692 |
| 2 | 3769 | 1615 | 2154 |
| 4 | 3230 | 1615 | 1615 |
| 2 | 2691 | 1615 | 1076 |
| 3 | 2153 | 1615 | 538 |
| 23 | 1615 | 1615 | 0 |

Subsequently, the temperature of the regeneration gas stream in flow direction immediately beyond the internal heating bed was adjusted to 550° C. and, while retaining this temperature, the composition and the magnitude of the regeneration gas stream and the exit pressure P (bar above atmospheric pressure) were changed in the sequence listed below in each case for a period t:

| Time t (min) | Regeneration gas stream (l (STP)/h) | Air stream content (l (STP)/h) | Nitrogen stream content (l (STP)/h) | P (bar gauge) |
|---|---|---|---|---|
| 156 | 1615 | 1615 | 0 | 3.5 |
| 1 | 0 | 0 | 0 | 0 |
| 9 | 108 | 108 | 0 | 0 |
| 114 | 1615 | 1615 | 0 | 3.5 |
| 10 | 1615 | 1615 | 0 | 0 |
| 170 | 1615 | 1615 | 0 | 3.5 |
| 5 | 1615 | 1615 | 0 | 0 |
| 180 | 1615 | 1615 | 0 | 3.5 |
| 10 | 1615 | 1615 | 0 | 0 |
| 170 | 1615 | 1615 | 0 | 3.5 |
| 10 | 1615 | 1615 | 0 | 0 |
| 170 | 1615 | 1615 | 0 | 3.5 |
| 10 | 1615 | 1615 | 0 | 0 |
| 170 | 1615 | 1615 | 0 | 3.5 |
| 10 | 1615 | 1615 | 0 | 0 |

-continued

| Time t (min) | Regeneration gas stream (l (STP)/h) | Air stream content (l (STP)/h) | Nitrogen stream content (l (STP)/h) | P (bar gauge) |
|---|---|---|---|---|
| 170 | 1615 | 1615 | 0 | 3.5 |
| 10 | 1615 | 1615 | 0 | 0 |
| 165 | 1615 | 1615 | 0 | 3.5 |
| 10 | 1615 | 1615 | 0 | 0 |
| 175 | 1615 | 1615 | 0 | 3.5 |
| 10 | 1615 | 1615 | 0 | 0 |
| 160 | 1615 | 1615 | 0 | 3.5 |
| 10 | 1615 | 1615 | 0 | 0 |
| 170 | 1615 | 1615 | 0 | 3.5 |
| 10 | 1615 | 1615 | 0 | 0 |
| 170 | 1615 | 1615 | 0 | 3.5 |
| 10 | 1615 | 1615 | 0 | 0 |
| 170 | 1615 | 1615 | 0 | 3.5 |
| 10 | 1615 | 1615 | 0 | 0 |
| 180 | 1615 | 1615 | 0 | 3.5 |
| 10 | 1615 | 1615 | 0 | 0 |
| 1280 | 1615 | 1615 | 0 | 2 |
| 5 | 1615 | 1615 | 0 | 0 |

During the last 5 minutes, the temperature of the regeneration gas stream in flow direction immediately beyond the internal heating bed was adjusted to 450° C.

Then, as the reducing gas, a mixture of 10.8 g/h of $H_2O$, 430 l (STP)/h of nitrogen and 430 l (STP)/h of hydrogen (purity >99.9% by volume) was obtained in the evaporator. The temperature of the reducing gas stream was adjusted to 450° C. in flow direction immediately beyond the internal heating bed. The reducing gas was conducted through the tubular reactor with an exit pressure of 2 bar above atmospheric pressure over a period of 45 minutes.

During the last 5 minutes, the temperature of the reducing gas stream in flow direction immediately beyond the internal heating bed was adjusted to 410° C.

Figure 4:
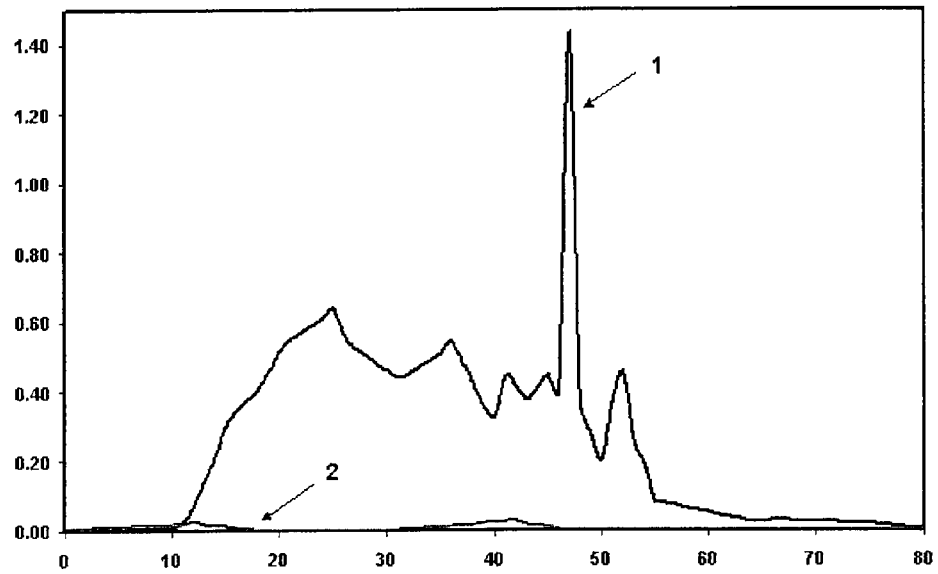
FIG. 4: contents in % by volume in the regeneration gas leaving the tubular reactor.

The dehydrogenation was then restarted in an identical manner. After an operating time of approx. 1 h, the (quasi-) steady operating state had been reestablished. Under the original operating conditions, the original value for G was attained again. The deactivation behavior of the regenerated catalyst bed corresponded to that of the freshly charged catalyst bed. During the overall regeneration process, the temperature in the tubular reactor was at values of ≦590° C. throughout. The profile of the content of $CO_2$ (1) and CO (2) in % by volume in the regeneration gas leaving the tubular reactor as the ordinate as a function of the regeneration time in minutes as the abscissa is shown by FIG. 4 (t=10 min=start of the supply of regeneration gas). The total content of carbon oxides in the regeneration gas leaving the tubular reactor was below 2% by volume over the entire regeneration time.

II. Comparative Example

The procedure was as in the example, except that the regeneration gas stream used was always a constant mixture of 5% by volume of molecular oxygen and 95% by volume of molecular nitrogen. The remaining boundary conditions (for example magnitude of the regeneration gas stream, exit pressure, temperature of the regeneration stream immediately beyond the internal heating bed) were retained identically. In the initial period of the regeneration, the total content of carbon oxides in the regeneration gas leaving the tubular reactor was above 5% by volume. After the dehydrogenation had been restarted, the original value for G was yet to be attained again under the original operating conditions in the steady operating state. Instead, only a G' (at the operating time to) of 16.3 mol % was achieved. The regenerated catalyst bed was deactivated more rapidly than in the case of the freshly charged catalyst bed.

III. Comparative Example

The procedure was as in the example, except that a gas mixture of 5% by volume of molecular oxygen and 95% by volume of molecular nitrogen was used within the first 60 minutes of the regeneration process (in the subsequent regeneration period, the regeneration gas composition corresponded in each case to that from the example). The remaining boundary conditions (for example magnitude of the regeneration gas stream, exit pressure, temperature of the regeneration gas stream immediately beyond the internal heating bed) were retained identically. In the initial period of the regeneration, the total content of carbon oxides in the regeneration gas leaving the tubular reactor was above 5% by volume.

After the dehydrogenation had been restarted, the original value for G was yet to be attained again under the original operating conditions in the steady operating state. Instead, only a G* (at the operating time $t_0$) of 16.7 mol % was achieved. The regenerated catalyst bed was deactivated more rapidly than in the case of the freshly charged catalyst bed.

U.S. Provisional Patent Application No. 60/888,366, filed Feb. 6, 2007, is incorporated in the present application by literature reference.

With regard to the abovementioned teachings, numerous changes and deviations from the present invention are possible.

It can therefore be assumed that the invention, within the scope of the appended claims, can be implemented differently than specifically described herein.

The invention claimed is:

1. A process for regenerating a catalyst bed deactivated in the course of a heterogeneously catalyzed partial dehydrogenation of a hydrocarbon to be dehydrogenated to a dehydrogenated hydrocarbon, which comprises, over a period t, the passage of a regeneration gas comprising molecular oxygen and inert gas but no hydrocarbon at elevated temperature through the deactivated catalyst bed with the proviso that the total content $G^A$ of carbon oxides in the regeneration gas passed through the catalyst bed, when it exits from the catalyst bed, is at least temporarily greater in the course of the regeneration over the period t than the corresponding content $G^E$, in each case expressed in % by volume of the regeneration gas volume, of the same regeneration gas passed through the catalyst bed when it enters the catalyst bed, and the difference $\Delta G = G^A - G^E$ passes through a maximum value $\Delta G^{max}$ by the end of the regeneration process, wherein
   a) 0.2% by volume $\leq \Delta G^{max} \leq$ 5% by volume and
   b) the content of molecular oxygen in the regeneration gas to be passed through the catalyst bed, expressed in % by volume of the regeneration gas volume, is increased at least three times during the period t up to the end of the regeneration process and each increase is at least 2% by volume.

2. The process according to claim 1, wherein 0.2% by volume $\leq \Delta G^{max} \leq$ 4% by volume.

3. The process according to claim 1, wherein 0.2% by volume $\leq \Delta G^{max} \leq$ 3% by volume.

4. The process according to any of claims 1 to 3, wherein the oxygen content of the regeneration gas to be passed through the catalyst bed is increased by at least 10% by volume in total within the period t.

5. The process according to any of claims 1 to 3, wherein the oxygen content of the regeneration gas to be passed through the catalyst bed is increased by at least 14% by volume in total within the period t.

6. The process according to claim 1, wherein the content of molecular oxygen in the regeneration gas to be passed through the catalyst bed on commencement of the process is $\leq$ 5% by volume.

7. The process according to claim 1, wherein the content of molecular oxygen in the regeneration gas to be passed through the catalyst bed on commencement of the process is $\leq$ 3% by volume.

8. The process according to claim 1, wherein the highest temperature T occurring within the period t in the catalyst bed, based on the highest temperature $T^{max}$ which occurred in the catalyst bed in the course of the heterogeneously catalyzed partial dehydrogenation which causes the deactivation of the catalyst bed, fulfils the following condition:

$$0.5 \cdot T^{max} \leq T \leq 1.5 \cdot T^{max}.$$

9. The process according to claim 1, wherein the loading B of the catalyst bed with regeneration gas is 1000 l (STP)/l·h $\leq B \leq$ 40 000 l (STP)/l·h.

10. The process according to claim 1, wherein the loading B of the catalyst bed with regeneration gas is 3000 l (STP)/l·h $\leq B \leq$ 20 000 l (STP)/l·h.

11. The process according to claim 1, wherein the loading B of the catalyst bed with regeneration gas passes through a maximum within the period t.

12. The process according to claim 1, wherein the regeneration gas comprises $N_2$ and/or $H_2O$ as inert gas.

13. The process according to claim 1, wherein at least a portion of the regeneration gas exiting from the catalyst bed is circulated and reused as a constituent of regeneration gas to be conducted freshly through the catalyst bed.

14. The process according to claim 13, wherein the content of CO in the regeneration gas to be conducted freshly through the catalyst bed is $\leq$ 3% by volume.

15. The process according to claim 1, which is performed at a working pressure of from 1 to 10 bar above atmospheric pressure.

16. The process according to claim 1, wherein the difference $T^A - T^E$ between the temperature of the regeneration gas on entry into the catalyst bed, $T^E$, and the temperature of the same regeneration gas on exit from the catalyst bed, $T^A$, is $\leq 250°$ C.

17. The process according to claim 1, wherein the catalyst bed is a fixed catalyst bed.

18. The process according to claim 17, wherein the bed volume of the fixed catalyst bed is $\geq$ 50 l and $\leq$ 10 000 m³.

19. The process according to claim 1, wherein the catalyst bed comprises catalysts which consist of at least one metal deposited on an oxidic support.

20. The process according to claim 18, wherein the at least one metal is a metal from the group consisting of Cu, Ag, Au, Zn, Cd, Hg, Ru, Rh, Pd, Os, Ir and Pt.

21. The process according to claim 1, wherein the catalyst bed is disposed in an adiabatic reactor.

22. A process for preparing acrolein and/or acrylic acid by heterogeneously catalyzed partial gas phase oxidation of propylene, comprising, as a first reaction stage, a heterogeneously catalyzed partial dehydrogenation of propane to propylene on a catalyst bed, which comprises regenerating the catalyst bed from time to time by a process according to claim 1.

* * * * *